(12) United States Patent
Decourtye et al.

(10) Patent No.: US 9,206,254 B2
(45) Date of Patent: Dec. 8, 2015

(54) METHOD AND KIT FOR DETECTING THE PREOVULATORY LH PEAK

(71) Applicant: ReproPharm, Nouzilly (FR)

(72) Inventors: Jeremy Decourtye, Saint Antoine du Rocher (FR); Laurence Dupuy, Villedomer (FR); Elodie Kara, Tours (FR); Marie-Christine Maurel, Tours (FR)

(73) Assignee: REPROPHARM, Nouzilly (FR)

( * ) Notice: Subject to any disclaimer, the term of this patent is extended or adjusted under 35 U.S.C. 154(b) by 0 days.

(21) Appl. No.: 13/861,980

(22) Filed: Apr. 12, 2013

(65) Prior Publication Data

US 2014/0134649 A1    May 15, 2014

Related U.S. Application Data

(60) Provisional application No. 61/623,447, filed on Apr. 12, 2012.

(51) Int. Cl.
| | |
|---|---|
| *G01N 33/53* | (2006.01) |
| *C07K 16/26* | (2006.01) |
| *G01N 33/68* | (2006.01) |
| *G01N 33/76* | (2006.01) |

(52) U.S. Cl.
CPC .............. *C07K 16/26* (2013.01); *G01N 33/689* (2013.01); *G01N 33/76* (2013.01); *C07K 2317/33* (2013.01)

(58) Field of Classification Search
None
See application file for complete search history.

(56) References Cited

U.S. PATENT DOCUMENTS

| 4,497,900 | A | * | 2/1985 | Abram et al. ................. 435/7.36 |
| 5,210,018 | A | * | 5/1993 | Nuzzolo et al. ............... 435/7.22 |
| 5,248,593 | A | * | 9/1993 | Hubner-Parajsz et al. ..... 435/7.9 |
| 5,998,130 | A | * | 12/1999 | Okayama et al. .................. 435/5 |
| 2011/0236911 | A1 | * | 9/2011 | Choo et al. .................... 435/7.91 |

OTHER PUBLICATIONS

Crowther (The Elisa guidebook, 2nd edition, 2009, p. 58-59).*
Loizou et al. (Clin. Exp. Immunol. 1985, vol. 62, p. 738-745).*

* cited by examiner

*Primary Examiner* — Jacob Cheu
(74) *Attorney, Agent, or Firm* — Arent Fox LLP

(57) ABSTRACT

The present invention relates to a method of detecting the preovulatory LH peak in a biological sample obtained from mammals and a kit for applying the method of detection.
The present invention finds application notably in the veterinary and medical areas.

18 Claims, 15 Drawing Sheets

A

B

A

B

A

B

A

B

A

B

A

B

Plasmas  0    5     0    5  ng/ml

AC1: anti-bovine LH    AC1: anti-porcine LH
AC2: HRP classical     AC2: HRP classical plasmas   0    6.2    0    6.2 ng/ml AC2 HRP classical    AC2 HRP new

METHOD AND KIT FOR DETECTING THE PREOVULATORY LH PEAK

CROSS-REFERENCE TO RELATED APPLICATION

This Application Claims the benefit of U.S. Provisional Application No. 61/623,447 filed on Apr. 12, 2012, the disclosure of which is hereby incorporated in its entirety by reference.

TECHNICAL FIELD

The present invention relates to a method of detecting the preovulatory LH peak in a biological sample obtained from mammals and a kit for applying the method of detection.

The present invention finds application notably in the medical and veterinary area.

In the following description, the references given in square brackets ([ ]) refer to the list of references given at the end of the text.

PRIOR ART

The ovulatory cycle in mammals involves a complex hormonal process involving in particular the hypophyseal gonadotropic hormones: luteinizing hormone (LH) and follicle-stimulating hormone (FSH).

In particular, the ovarian cycle comprises two phases: the follicular phase (growth of the follicle and maturation of the oocyte) leading to ovulation, a period favorable to fertilization, and the luteal phase (formation of the corpus luteum). FSH is responsible for growth and maturation of the preovulatory follicle and LH induces the terminal follicular growth of the latter and ovulation. In particular, prior to ovulation, LH and FSH increase significantly in the plasma up to a peak, following which ovulation occurs. For each mammalian species, ovulation occurs at a very precise and constant moment after the LH peak between 12 and 52 hours after the LH peak depending on the species, 24 hours in the cow, ewe, goat, woman and 48 hours in the sow and the bitch. It is therefore necessary and important to have at our disposal a test for detecting the preovulatory LH peak that is robust and can be used in the conditions of animal husbandry as well as being suitable for human use for women. This test for detecting the preovulatory LH peak will make it possible to predict the best moment for artificial insemination, for example.

A test exists at present for detecting ovulation for the dog and the cat, the Witness® LH test (registered trademark, marketed by the company Synbiotics corporation). It is based on detection of LH and is performed on the basis of the serum only. However, this test is not 100% reliable and the results obtained sometimes include a significant number of false positives.

There are also, for human beings of the female sex, ovulation tests based, for example, on an agglutination reaction DISCRETEST (registered trademark, marketed by the company CHEFARO ORGANON), or tests based on an immunoenzyme reaction, for example the Clearblue test, Digital Ovulation Test. These tests are of the Lateral Flow type and are in the form of a strip, for example, the QuickTest™ (registered trademark), Babyprep Ovulation Test, or in the form of a pen or cassette, for example Polidis, Première Réponse [First Response], Conceive, Digitest. They are all performed with urine and make it possible to detect the presence (appearance of two colored bands) or the absence of LH (appearance of a single colored band). However, interpretation of the results obtained can be ambiguous, namely whether there is presence or absence of a second colored band, and gives a significant number of false negatives or false positives. In this case, these methods lead to a poor interpretation and do not allow accurate determination of when ovulation will occur.

Moreover, as these tests are all based on urine, they are difficult to apply for mammals such as pigs, sheep, bovines, goats or else require the presence of a person to collect the urine from the mammal, which involves additional cost.

Two other types of tests exist for women; one is based on measurement of the pH of the skin via the sweat by a microprocessor kept in close contact with the skin by a scratch bracelet worn on the wrist (OV-Watch® (registered trademark) and the other is based on observation, with a small microscope, of dried saliva, which forms different patterns (observed with the microscope) depending on the level of estrogens secreted during a menstrual cycle (donnaTEST® (registered trademark). These two devices are expensive and require special equipment (bracelet or small microscope) and are unsuitable for animals or for easy use for women. Moreover, donnaTEST® (registered trademark) requires conducting the examination on perfectly clean saliva, taken while fasting, which is impossible with animals. Moreover, the parameters measured (pH, level of estrogens) are less accurate than the preovulatory LH peak for reliable dating of ovulation to within 12 hours.

Moreover, the methods known in the prior art for human beings are not directly applicable to other mammals, because of the different specificities of the antibodies used and/or the prohibitive cost involved.

There is therefore a real need to find a method and a test that overcome these shortcomings, drawbacks and obstacles of the prior art, in particular a method of detecting the LH peak in any mammal with increased specificity and sensitivity. Moreover, there is a real need to find a method permitting interpretation of the result unambiguously and that is reliable over time. Furthermore, there is also a real need to find a method/test making it possible to reduce the costs of the methods for detecting the LH peak and of being adapted to animal husbandry conditions. In particular, there is a real need to find a method/test that can use biological media such as blood, vaginal mucus, nasal mucus, saliva, urine or milk, and not requiring detection times that are too precise.

DESCRIPTION OF THE INVENTION

The present invention aims to overcome the drawbacks of the prior art by providing a method of detecting the preovulatory LH peak in a biological sample obtained from mammals and comprising the following steps:
  a. fixing an anti-LH antibody on a test surface;
  b. contacting the test surface on which said anti-LH antibody is fixed with a buffer solution comprising 5 to 50 vol % of fetal calf serum;
  c. contacting said surface obtained in step (b) with a biological sample;
  d. after step (c), rinsing the test surface in a washing solution;
  e. contacting the test surface rinsed in step (d) with a buffer solution of conjugate comprising an enzyme-coupled anti-LH antibody and from 5 to 50 vol % of fetal calf serum;
  f. after step (e), rinsing the test surface in a washing solution; and
  g. after step (f), contacting the test surface with a solution comprising a substrate of said enzyme.

The method of the invention makes it possible to detect the preovulatory LH peak with a specificity and a sensitivity close to 100% of those of a quantitative assay. The inventors discovered that the method of the invention makes it possible to obtain results without false positives.

Moreover, the inventors found that the method of the invention allows detection of the LH peak via coloration of the test surface by the substrate of the enzyme and that this coloration is stable over time.

The inventors also found that the intensity of coloration of the test surface by the substrate is proportional to the LH concentration.

The method of the invention therefore advantageously allows accurate determination of the threshold value of the LH concentration, for example making it possible to accurately determine when ovulation will occur.

The method of the invention also makes possible, advantageously, from the coloration of the test surface, visual detection of the LH peak, not requiring a special device for detection and reading.

According to the invention, preovulatory LH peak means the peak of luteinizing hormone (LH) that initiates rupture of the ovulatory follicle and causes ovulation. This corresponds for example to an LH concentration in a biological fluid above 0.5 ng/ml, for example in the cow to a plasma LH concentration above 2 ng/ml, and for example in the sow to a plasma LH concentration above 0.5 ng/ml.

According to the invention, mammal means a mammal selected from the group comprising the order Monotremata, Didelphimorphia, Paucituberculata, Microbiotheria, Notoryctemorphia, Dasyuromorphia, Peramelemorphia, Diprotodontia, Tubulidentata, Sirenia, Afrosoricida, Macroscelidea, Hyracoidea, Proboscidea, Cingulata, for example the armadillo, Pilosa, Scandentia, Dermoptera, Primates, Rodentia, Lagomorpha, Erinaceomorpha, Soricomorpha, Chiroptera, Pholidota, Carnivora, Perissodactyla, Artiodactyla and Cetacea.

It can be for example a human or an animal. It can be for example a farm animal, a pet, an endangered animal species or any other animal whose controlled reproduction is of interest.

For example, the farm animal can be selected from the group comprising bovines, pigs, sheep, goats, camelids, canines, equines, murines. For example, the pet can be selected from the group comprising canines and felines.

According to the invention, the mammal can be, for example, a mammal previously treated to stimulate ovulation, for example with a "superovulation" treatment as described in the references "Use of Norgestomet implant as an aid when superovulating low fertility dairy cattle", Ellington J E, Elefson E E, McCall R M. *Theriogenology,* 1987; 27, 227 [7] and "The production of embryos in bovines: research trends for increasing the efficacy of superovulation treatments", Saumande J. *INRA Productions Animates,* 1995; 8(4), 275-283 [6].

According to the invention, "test surface" means a flat or curved or rough surface.

According to the invention, the test surface can be a surface selected from a plastic surface, for example a plastic polymer, a glass surface, a polymethylacrylate surface, a polystyrene surface. Preferably, the test surface is a plastic surface, for example thermoplastic or thermosetting. It is preferably a surface having very low nonspecific coupling characteristics. It can be for example the MediSorp™ (brand name), MaxiSorp™ (brand name), MultiSorp™ (brand name), MiniSorp™ (brand name) or CovaLink™ (brand name) surface.

According to the invention, the test surface can be for example a rectangular surface and/or any surface suitable for carrying out the method. It can be for example a spatula, a stick, a rod or any other support suitable for carrying out the present invention. It can be for example a stick with fins, for example the immunostick marketed by the company NUNC (Nunc Immuno™ Stick (brand name)).

According to the invention, "biological sample" means a liquid or solid sample. According to the invention, the sample can be any biological fluid, for example it can be a sample of blood, of plasma, of serum, of vaginal mucus, of nasal mucus, of saliva, of urine and/or of milk. Preferably the biological sample is a blood sample or a sample of vaginal mucus.

According to the invention, the sample can be a sample previously taken from said mammal.

According to the invention, step a) of fixation of an anti-LH antibody on a test surface can be carried out by any method known by a person skilled in the art. For example it can be a method described in "Enzyme-linked immunosorbent assay (ELISA). Quantitative assay of immunoglobulin G", Engvall, E. and Perlman, P., *Immunochemistry,* 1971 September; 8(9): 871-4 [1]; "Techniques Immuno-enzymatiques" Thérèse Ternynck and Stratis Avrameas, éditions INSERM, 1987 [1]; "Immunobiology" Charles A. Janeway, Paul Travers, Pierre L. Masson—2003—Medical; Janeway's Immunobiology, Kenneth Murphy, Paul Travers, Mark Walport, 2011, éditions GS) [2].

According to the invention, the anti-LH antibody can be produced by any method known by a person skilled in the art, for example the method described in the bibliographical reference, for example a method described in "Radio-immunoassay of plasma luteinizing hormone in the sheep. Development of the assay technique", Pelletier J., Kann G., Dolais J., Rosselin G., *C. R. Acad. Sc. Paris,* 1968 June; 266: 2291-2294 [5]. It can be for example a method comprising immunization of a suitable animal using an antigen, for example a purified LH and/or a commercially available anti-LH antibody.

According to the invention, the anti-LH antibody can be an antibody produced in the rabbit, sheep, goat, equine, bovine, mouse, rat. Preferably, the anti-LH antibody is an antibody obtained from a rabbit.

According to the invention, the anti-LH antibody fixed on the test surface can be a polyclonal or monoclonal antibody. It can be an antibody directed against any mammalian LH, for example it can be an anti-LH antibody selected from an anti-bovine LH antibody, an anti-porcine LH antibody, an anti-ovine LH antibody, an anti-caprine LH antibody, an anti-canine LH antibody, an anti-feline LH antibody, an anti-equine LH antibody, an anti-camelid LH antibody, an anti-human LH antibody.

Preferably, the anti-LH antibody is a polyclonal anti-bovine LH antibody, or a polyclonal anti-porcine LH antibody for example the anti-bovine LH antibody produced in the rabbit by the company Eurogentec (Belgium) according to the method "Standard antiprotein packages 28-day Speedy in Rabbit" (brand name), the anti-porcine LH antibody can be produced for example by immunization of rabbits according to the method described for example in the reference "Radioimmunoassay of the plasma luteinizing hormone in the sheep. Development of the assay technique", Pelletier J., Kann G., Dolais J., Rosselin G., *C. R. Acad. Sc. Paris,* 1968 June; 266: 2291-2294 [5]. It can be for example a method comprising for example three injections of 200 μg of purified porcine LH carried out every two weeks, followed by ten boosters with 100 μg of purified LH carried out every five weeks. Blood samples were taken six and nine days after each booster.

These rabbit antibodies were purified for example by affinity chromatography on Protein A Sepharose gel according to the method described in "Techniques Immuno-enzymatiques" Therese Ternynck and Stratis Avrameas, editions INSERM, 1987 [1].

The inventors discovered, unexpectedly, that the anti-bovine LH antibody and the anti-porcine LH antibody also allow detection of LH of other mammals, for example bovine LH, porcine LH, ovine LH, caprine LH while maintaining sufficient specificity and sensitivity for the method of detecting the preovulatory LH peak in these different species.

According to the invention, step b) of contacting a test surface on which said anti-LH antibody is fixed, with a buffer solution comprising 5 to 50 vol % of fetal calf serum can be performed by immersing said test surface in said buffer, by spraying the test surface with said buffer solution.

According to the invention, step b) of contacting a test surface on which said anti-LH antibody is fixed, with a buffer solution comprising 5 to 50 vol % of fetal calf serum can be performed for a time greater than 30 minutes, for example from 30 minutes to 18 hours, for example from 1 to 18 hours.

According to the invention, the buffer solution comprising 5 to 50 vol % of fetal calf serum can be selected from the group comprising a phosphate buffer saline solution (PBS), a saline Tris buffer solution (TBS), pH 7.4. Preferably the buffer solution comprising from 5 to 50 vol % of fetal calf serum is a $K_2HPO_4/KH_2PO_4$ 0.01 M-NaCl 0.15M (PBS) buffer solution pH 7.4.

According to the invention, the fetal calf serum can be commercially available fetal calf serum, for example it can be fetal calf serum (FCS) marketed by the company Lonza under the reference 14-801 F.

According to the invention, the percentage by volume of fetal calf serum in the buffer solution in step b) can be from 5 to 50 vol %, preferably from 20 to 50 vol %.

According to the invention, step c) of contacting said surface obtained in step (b) with a biological sample can be performed by immersing said test surface in said sample, by spraying the test surface with said sample. According to the invention, step c) of contacting said surface obtained in step (b) with a biological sample can be performed for a time greater than 5 minutes, for example from 5 to 60 minutes, for example for 15 minutes.

According to the invention, biological sample means a liquid or solid sample. According to the invention, the sample can be derived from any biological fluid, for example it can be a sample of blood, of plasma, of serum, of vaginal mucus, of nasal mucus, of saliva, of urine and/or of milk.

According to the invention, when the biological sample is blood, the contacting step can be performed by immersing the biological sample and the test surface in a solution comprising heparin.

According to the invention, steps (d) and (f) of rinsing said surface obtained in step (c) or (e) with a washing solution can be performed by immersing said test surface in said washing solution, by spraying the test surface with said washing solution According to the invention, steps (d) and (f) of rinsing said surface obtained in step (c) or (e) with a washing solution can be performed for a time from 2 to 30 seconds, for example from 5 to 25 seconds, for example from 10 to 20 seconds.

According to the invention, the washing solution can be any washing solution known by a person skilled in the art and that is suitable, for example it can be a solution selected from the group comprising a Tris buffer saline (TBS), a phosphate-buffered saline (PBS), for example PBS pH 7.4 $K_2HPO_4/KH_2PO_4$ 0.01 M-NaCl 0.15M, or water.

According to the invention, the washing solution used in steps (d) or (f) can be identical or different.

According to the invention, step (e) of contacting a test surface with a buffer solution of conjugate comprising an enzyme-coupled anti-LH antibody and from 5 to 50 vol % of fetal calf serum can be performed by immersing said test surface in said sample, by spraying the test surface with said sample.

According to the invention, step e) of contacting said surface can be performed for a time greater than 5 minutes, for example from 5 to 60 minutes, for example for 15 minutes.

According to the invention, the buffer solution of conjugate comprising an enzyme-coupled anti-LH antibody and from 5 to 50 vol % of fetal calf serum can be selected from the group comprising a phosphate buffer saline solution (PBS), a saline Tris buffer solution (TBS), pH 7.4. Preferably the buffer solution of conjugate is a $K_2HPO_4/KH_2PO_4$ 0.01 M-NaCl 0.15M (PBS) buffer pH 7.4.

According to the invention, the enzyme-coupled anti-LH antibody can be a polyclonal or monoclonal antibody. According to the invention, the enzyme-coupled anti-LH antibody can be a rabbit, sheep, goat, equine, bovine, mouse, or rat antibody. For example, the enzyme-coupled anti-LH antibody can be an equine anti-LH antibody, for example a horse antibody.

According to the invention, the enzyme-coupled anti-LH antibody can be an antibody directed against any mammalian LH, for example it can be an anti-LH antibody selected from an anti-bovine LH antibody, an anti-porcine LH antibody, an anti-ovine LH antibody, an anti-caprine LH antibody, an anti-canine LH antibody, an anti-feline LH antibody, an anti-equine LH antibody, an anti-camelid LH antibody, an anti-human LH antibody. It can be for example an anti-canine LH antibody, for example the antibody marketed by the company Millipore under the catalog reference AB944.

According to the invention, the anti-LH antibody is coupled to an enzyme selected from the group comprising peroxidase, beta-galactosidase, glucose oxidase and alkaline phosphatase. The enzyme is preferably peroxidase, for example a peroxidase with heme or a peroxidase without heme. It can be for example a horseradish peroxidase marketed by the company Sigma under the catalog reference P6782.

According to the invention, the buffer solution of conjugate can be prepared prior to or concomitantly with application of the method of the invention.

According to the invention, step (g) of contacting the test surface obtained in step (f) with a solution comprising a substrate of the enzyme can be performed by immersing said test surface in said solution comprising a substrate of the enzyme, by spraying the test surface with said solution comprising a substrate of the enzyme.

According to the invention, step (g) of contacting said surface can be performed for a time greater than 5 minutes, for example from 5 to 15 minutes According to the invention, the solution comprising a substrate of the enzyme can be a buffer solution, for example a saline Tris buffer solution (TBS), a phosphate buffer ($K_2HPO_4/KH_2PO_4$ 0.01 M pH 7.4), a phosphate buffer saline solution (PBS), for example PBS pH 7.4 ($K_2HPO_4/KH_2PO_4$ 0.01 M-NaCl 0.15M), water, a citrate buffer, for example citrate ($NaCH_3CO_2$) from 0.003 to 0.3M adjusted to pH5 with acetic acid ($CH_3COOH$). Preferably, the solution comprising a substrate of the enzyme is a citrate ($NaCH_3CO_2$) buffer solution at 0.03M adjusted to pH5.

According to the invention, the substrate can be selected from the group comprising 3,3',5,5'-tetramethylbenzidine (also called Membrane TMB), 4-chloro-1-naphtho/3,3'-diaminobenzidine tetrahydrochloride (also called CN/DAB), 3-amino-9-ethylcarbazole (also called AEC), 3,3-dimethoxybenzidine-o-dianisidine (also called ODN), 5-bromo-4-chloro-3'-indolyl phosphate p-toluidine salt (also called BCIP), a mixture of nitro-blue tetrazolium chloride (also called NBT) and of 5-bromo-4-chloro-3'-indolyl phosphate p-toluidine salt (also called BCIP), the mixture Naphthol As-Mx phosphate and 4-chloro-2-methylbenzenediazonium salt (also called Fast red TR salt), the mixture Naphthol As-Mx phosphate and diazotized salt of 4'-amino-2',5'-diethoxybenzanilide zinc chloride (also called Fast blue BB salt), 5-iodo-3-indolyl-β-D-galactopyranoside (also called Purple-Gal), 5-bromo-6-chloro-3-indolyl-β-D-galactopyranoside (also called Red-Gal), 6-chloro-3-indolyl-β-D-galactopyranoside (also called Rose-Gal), 5-bromo-3-indolyl-β-D-galactopyranoside (also called Blue-Gal), N-methylindolyl-β-D-galactopyranoside (also called Green-Gal).

Preferably, the substrate is Membrane TMB, preferably the Membrane TMB marketed by the company KPL under the reference 50-77-18 or by the company Sigma under the reference T0565.

According to the invention, the substrate can be diluted in said buffer solution with a dilution factor from ½ to 1/20. Preferably, the dilution of the substrate is from ½ to ⅛, or equal to ½.

Advantageously, dilution of the substrate, for example of Membrane TMB, makes it possible to increase the visibility for detecting the LH peak by increasing the intensity of coloration of the test surface.

According to the invention, the method of the invention can also comprise, after at least one or all of the rinsing steps, a drying step. This can be, for example, incubation of the test surface in a stove at a temperature from 25 to 37° C., for example at 37° C.

According to the invention, the drying step can be performed for a time from 0.5 to 5 hours, for example 3 hours.

According to the invention, steps a) and b) of the method can be performed beforehand in order to have a "ready-to-use" test surface.

The present invention also relates to a kit for applying the method of the invention, comprising a support having a test surface on which anti-LH antibodies are fixed, a PBS buffer, a buffer solution of conjugates comprising fetal calf serum and an enzyme-coupled anti-LH antibody, and a development buffer solution comprising a substrate of said enzyme.

According to the invention, the buffer solution of conjugates is as defined previously.

According to the invention, the fixed anti-LH antibodies are as defined previously.

According to the invention, the enzyme-coupled anti-LH antibodies are as defined previously. Advantageously, the enzyme-coupled anti-LH antibody is a peroxidase-coupled anti-LH antibody.

According to the invention, the detection solution is as defined previously.

According to the invention, the substrate of the enzyme is as defined previously. Advantageously, the substrate of the enzyme is Membrane TMB.

According to the invention, the substrate of the enzyme, on oxidation, advantageously permits coloration of the test surface and thus detection of the preovulatory LH peak.

Advantageously, the method of the invention and the kit for application thereof permit accurate, semi-quantitative detection of the LH present in the biological fluid. In particular, according to the invention, the intensity of coloration of the test surface obtained is proportional to the LH concentration.

Advantageously, according to the invention, the substrates used, for example Membrane TMB, permit coloration and preservation of the coloration on the test surface after application of the method.

Advantageously, the method of the invention permits visual detection of the LH peak and does not require a special device, for example an optical device.

Advantageously, the method and the kit of the invention make it possible to detect very easily, on the farm, the preovulatory LH peak and constitute a tool for improving artificial insemination practice in animals. For example, in animals, it is a tool for predicting the moment of ovulation (occurring 24 hours after the LH peak) thus permitting better planning of the act of artificial insemination, for example 12 hours after the LH peak.

The method and the kit of the invention can thus be used advantageously as aid/supplement to superovulation treatments to optimize fertilization and obtain a large number of mammalian embryos. Moreover, this optimization advantageously makes it possible to increase the number of good-quality, transferable embryos.

Other advantages may become apparent to a person skilled in the art on reading the following examples, illustrated by the appended figures, given for purposes of illustration.

BRIEF DESCRIPTION OF THE FIGURES

FIG. 1 B shows a bar chart or histogram of the intensity of the color obtained on the sticks in units of density as a function of the LH concentration in the plasmas.

FIG. 2 B shows a bar chart of the intensity of the color obtained on the sticks in units of density as a function of the LH concentration in the plasmas.

FIG. 3 B shows a bar chart of the intensity obtained on the sticks in units of density as a function of the LH concentration in the plasmas.

FIG. 5 B shows a photograph of sticks after application of the method of the invention with the same bovine plasmas comprising different concentrations of LH, namely 0, 1, 2, 5 and 10 ng/ml after detection with ELISA TMB.

FIG. 5 C shows a bar chart of the intensity of the color obtained on the sticks in units of density as a function of the LH concentration in the plasmas. The bars marked with large-square checker represent the intensity of the color obtained with ELISA TMB. The bars marked with small-square checker represent the intensity of the color obtained with Membrane TMB.

FIG. 6 B shows a bar chart of the intensity of the color obtained on the sticks in units of density as a function of the different substrates of the enzyme peroxidase: 3,3'-diaminobenzidine tetrahydrochloride (DAB), 4-chloro-1-naphthol (CN), 4-chloro-1-naphtho/3,3'-diaminobenzidine tetrahydrochloride (CN/DAB), ortho-phenylenediamine (OPD), the Membrane TMB marketed by the company KPL (TMB KPL) or by the company Sigma (TMB Sigma).

FIG. 7 B shows a bar chart of the intensity of the color obtained on the sticks in units of density as a function of the different substrates of the enzyme: 3,3'-diaminobenzidine tetrahydrochloride (DAB), 4-chloro-1-naphthol (CN), 4-chloro-1-naphtho/3,3'-diaminobenzidine tetrahydrochloride (CN/DAB), ortho-phenylenediamine (OPD), 3,3-dimethoxybenzidine-o-dianisidine (ODN), 3-amino-9-ethylcarbazole (AEC), the Membrane TMB marketed by the company KPL (TMB KPL) or by the company Sigma (TMB Sigma).

FIG. 19 B shows a diagram of the value of the plasma LH concentration in ng/ml as a function of the sampling hour.

FIG. 20 B shows the value of the plasma LH concentration in ng/ml as a function of time in hours on the thirteenth day (D13) and fourteenth day (D14) of the cycle.

FIG. 21 B shows the plasma LH concentration in ng/ml as a function of time in hours on the third day (D3), fourth day (D4) and fifth day (D5) after weaning.

FIG. 22 B shows the plasma LH concentration in ng/ml as a function of time in hours on the third day (D3), fourth day (D4) and fifth day (D5) after weaning.

EXAMPLES

Example 1

Method of Detecting an LH Peak

Figure 1:
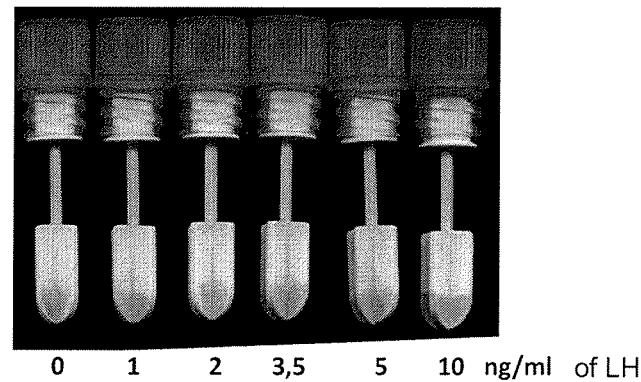
FIG. 1 A shows a photograph of sticks after application of the method of the invention with bovine plasmas comprising different concentrations of LH, namely 0, 1, 2, 3.5, 5 and 10 ng/ml, the sticks having been coated beforehand with PBS buffer solution.
Figure 1:
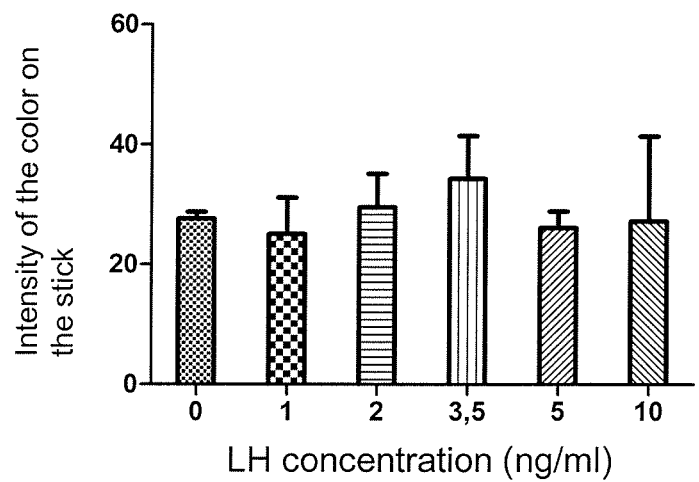

In this example, the test surface used is a plastic surface of a stick marketed by the company NUNC (Immuno™ Stick Nunc, Maxisorp).

On the test surface, an anti-LH antibody was fixed by coating with 250 µl of rabbit anti-bovine LH antibody obtained after purification on a Protein A Sepharose column from a serum of rabbit immunized with purified bovine LH called hereinafter AC1 prepared at 20 µg/ml in $NaHCO_3$/$Na_2CO_3$ buffer 0.1M pH 9.6 containing 0.05 vol % of Pro-Clin300 (registered trademark) marketed by the company Sigma-Aldrich, ref. 48912-U. The surface was then incubated for 1 hour at 37° C., then 18 hours at 4° C.

The surface was then dried by shaking to remove the residue of the liquid of AC1.

The test surface on which the antibody is fixed was brought into contact, via "surcoating" of the surface, with 900 µl of PBS with addition of fetal calf serum (FCS) 50 vol % (Lonza, reference 14-801 F) for 1 hour at 37° C. Said surface obtained was then dried by shaking and was dried in a vertical position in a stove at 37° C. for 3 hours.

The surface obtained was contacted with a sample of 250 µl of blood by immersion in a heparinized tube (NUNC polypropylene cryotube, ref. 368632). The heparinized tube was treated beforehand with 12 µl of a heparin solution at 500 IU/ml prepared from Choay Heparin marketed by Sanofi Aventis and diluted in PBS filtered on a filter with porosity of 0.2 µm (Millipore, ref. GSWP04700), and then dried for 3 hours in a stove at 37° C.

The test surface was then rinsed in 30 mL of a washing solution, namely a phosphate buffer saline solution PBS pH 7.4 $K_2HPO_4$/$KH_2PO_4$ 0.01 M-NaCl 0.15M contained in a 40 ml tube.

The rinsed test surface obtained was contacted in a cryotube (marketed by the company NUNC, ref. 368632) with 300 µl of a buffer solution of conjugate comprising a horse anti-ovine LH antibody coupled to horseradish peroxidase (HRP) prepared according to the method described in "Techniques Immuno-enzymatiques" (Therese Ternynck and Stratis Avrameas, editions INSERM, 1987) called hereinafter AC2 HRP at 10 µg/ml in PBS FCS 50 vol % containing 0.05 vol % of ProClin300 (registered trademark) previously prepared. It was in particular the antibody AC2 HRP produced in the horse described in French patent No. FR90 06863, patent No. FR 2 662 804.

The test surface was then rinsed in 30 mL of a washing solution, namely a phosphate buffer saline solution PBS pH 7.4 $K_2HPO_4$/$KH_2PO_4$ 0.01 M-NaCl 0.15M contained in a 40 ml tube.

The rinsed test surface obtained was contacted for 15 minutes in a cryotube marketed by the company NUNC, ref. 368632 with a solution comprising a substrate of horseradish peroxidase (HRP) namely 300 µL of Membrane TMB (marketed by the company KPL, ref. 50-77-18) diluted to 50% in citrate buffer ($NaCH_3CO_2$) 0.03M adjusted to pH5 with acetic acid ($CH_3COOH$).

The surface obtained was then withdrawn from the tube and visual observation of the blue coloration of the test surface was carried out, and showed the presence of LH in the sample tested.

As demonstrated in this example, the method of the invention advantageously makes it possible to detect the presence of LH in a biological sample.

Example 2

Comparative Tests with Different Constituents

In this example, the products/methods used are those in example 1 except for the following elements.

1. Test of "Surcoating" Buffers and Preparation of the Enzyme-Coupled Antibody (AC2-HRP)

Three buffers were tested:
PBS pH 7.4 ($K_2HPO_4$/$KH_2PO_4$ 0.01 M-NaCl 0.15M) (VWR, ref. 26930.293, 26936.293, 27810.295)
PBS comprising 20 vol % of FCS (fetal calf serum) (Lonza, reference 14-801F)
PBS comprising 50 vol % of hypophysectomized ram serum (INC medium—patent application No. FR90 06863, INRA/CNRS, patent No. FR 2 662 804).

These three buffers were used for contacting the test surface for "surcoating" and for diluting the peroxidase-coupled anti-ovine LH antibody, AC2-HRP namely an anti-LH antibody purified on a Protein G Sepharose column from a serum of horse immunized against the ovine LH and coupled to peroxidase (Sigma, reference P6782). It was in particular the antibody AC2 HRP produced in the horse described in French patent No. FR90 06863, patent No. FR 2 662 804.

The conditions for manufacture of the stick are those described above.

Each of the three sets of conditions was evaluated on 6 plasmas taken serially from one and the same cow at the time of the preovulatory LH peak. These plasmas were assayed quantitatively beforehand by the ELISA method, with the kit LH DETECT (registered trademark) (ReproPharm SA, France). Their LH concentrations were respectively 1-2-3.5-5 and 10 ng/ml. These experiments were repeated between three and five times. In each experiment, the visual reading of the results was validated by quantification of the color obtained on the sticks. For this, the sticks are scanned using an EPSON Scanner (Perfection 1200 PHOTO) and then the intensity of the color obtained on each of them is quantified by densitometry with the "Scion Image" software (Scion Incorporation). This quantification is expressed in units of density. The results were compared statistically by single-factor analysis of variance followed by a Bonferroni test or by the Kruskal-Wallis test using the GraphPad Prism software, version 5.

The results obtained with PBS are presented in FIG. 1 and in Table 1 below. FIG. 1 A shows a photograph of sticks after application of the method of detection with cow plasmas comprising different concentrations of LH, namely 0, 1, 2, 3.5, 5 and 10 ng/ml, the sticks having been coated beforehand with PBS buffer solution. FIG. 1 B shows a bar chart of the intensity of the color obtained on the sticks in units of density as a function of the LH concentration. As shown in FIG. 1A, a deep blue color is observed on all the sticks regardless of the LH concentration of the plasma. A strong colored signal was also observed with the negative plasma (0 ng/ml of LH), which is reflected in a strong nonspecific signal, which is very unfavorable in development of the test.

TABLE 1 intensity of the color as a function of the LH concentration with PBS buffer

| LH concentration | Intensity of the color (units) | |
|---|---|---|
| (ng/ml) | Mean value | Standard deviation |
| 0 | 27.7 | 1.09 |
| 1 | 25.14 | 6.04 |
| 2 | 29.59 | 5.5 |
| 3.5 | 34.28 | 7.18 |
| 5 | 26.11 | 2.75 |
| 10 | 27.21 | 14.16 |

As demonstrated in this example, the color that appeared on the stick is uniform but is independent of the LH concentration (FIG. 1A). The plasma without LH (0 ng/ml) gives a strong color and is evidence of a strong nonspecific signal. There is no significant difference between the sticks when PBS buffer is used for coating the test surface and for diluting the enzyme-coupled anti-LH antibody.

Figure 2:
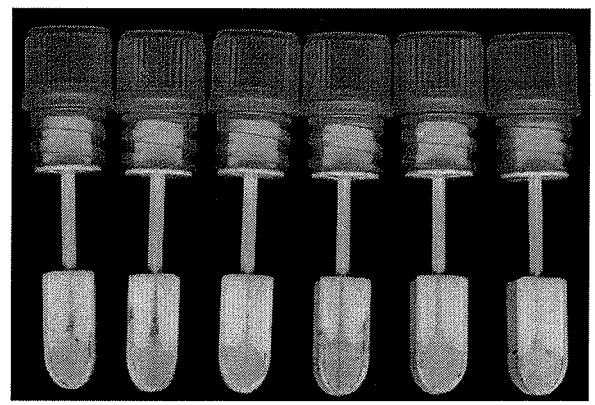
FIG. 2 A shows a photograph of sticks after application of the method of the invention with bovine plasmas comprising different concentrations of LH, namely 0, 1, 2, 3.5, 5 and 10 ng/ml, the sticks having been coated beforehand with PBS buffer solution comprising 50% of hypophysectomized ram serum.
Figure 2:
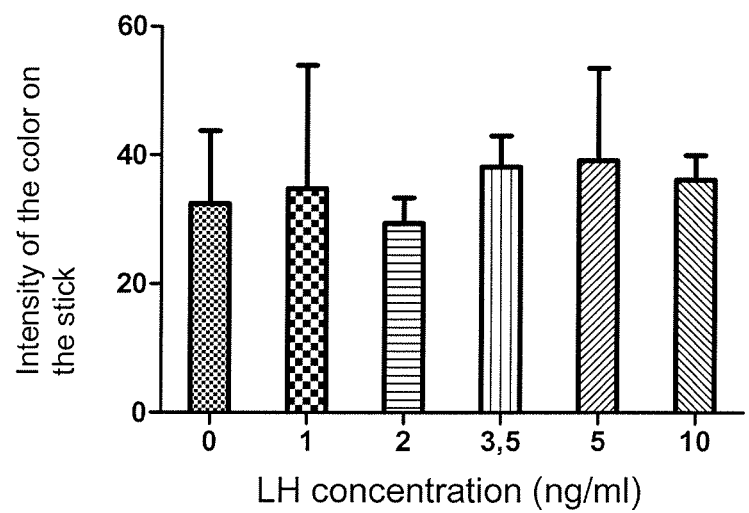

The results obtained with a PBS comprising hypophysectomized ram serum are presented in FIG. 2 and in Table 2 below. FIG. 2A shows a photograph of sticks after application of the method of the invention with solutions comprising different LH concentrations, namely 0, 1, 2, 3.5, 5 and 10 ng/ml, the sticks having been coated beforehand with PBS buffer solution comprising 50 vol % of hypophysectomized ram serum. FIG. 2B shows a bar chart of the intensity of the color obtained on the sticks in units of density as a function of the LH concentration. As shown in FIG. 2A and on the diagram in FIG. 2B, a very strong nonspecific interference is observed, reflected in sticks colored at the same intensity regardless of the LH concentration of the plasma assayed.

The visual interpretation (FIG. 2A) was validated by quantification of the color intensity measured by scanning (FIG. 2B and Table 2). There is no significant difference between the samples regardless of their LH concentration.

TABLE 2 color intensity as a function of the LH concentration with PBS buffer comprising hypophysectomized ram serum

| LH concentration | Color intensity (units of density) | |
|---|---|---|
| (ng/ml) | Mean value | Standard deviation |
| 0 | 32.48 | 11.37 |
| 1 | 34.77 | 19.16 |
| 2 | 29.47 | 3.92 |
| 3.5 | 38.11 | 4.84 |
| 5 | 39.11 | 14.36 |
| 10 | 36.10 | 3.8 |

As demonstrated in this example, the color that appeared on the stick is very strong regardless of the LH concentration in the samples. A strong nonspecific signal was obtained with the plasma without LH (0 ng/ml). As shown in FIG. 2B and Table 2: there is no significant difference between the color intensity measured on the different sticks when PBS buffer comprising hypophysectomized ram serum is used for coating the test surface and for diluting the enzyme-coupled anti-LH antibody.

All these results therefore clearly show that PBS alone or comprising hypophysectomized ram serum are not suitable buffers and do not allow visual reading.

The results obtained with PBS comprising 20 vol % of FCS as "surcoating" buffer and for preparing the enzyme-coupled antibody, here AC2 HRP are presented in FIGS. 3A and 3B. FIG. 3A shows a photograph of sticks after application of the method of the invention with solutions comprising different concentrations of LH, namely 0, 1, 2, 3.5, 5 and 10 ng/ml, the sticks having been coated beforehand with PBS buffer solution comprising 20 vol % of fetal calf serum. FIG. 3B shows a bar chart of the intensity of the color obtained on the sticks in units of density as a function of LH concentration. As shown in FIGS. 3A and 3B and in Table 3 below, the color intensity is proportional to the LH concentration. Appearance of a definite blue color, detectable by eye starting from 2 ng/ml (FIG. 3A), is observed. This visual reading is validated by quantification of the color of the sticks carried out by means of a scanner (FIG. 3B and Table 3). Statistical analysis by the Bonferroni test showed that appearance of the color is significant starting from a concentration of 2 ng/ml, which represents the threshold defining the start of the preovulatory LH peak ($p<0.001$).

TABLE 3 color intensity as a function of LH concentration with PBS buffer comprising fetal calf serum at 20 vol %

| LH concentration | Color intensity (units of density) | |
|---|---|---|
| (ng/ml) | Mean value | Standard deviation |
| 0 | 4.58 | 0.59 |
| 1 | 12.02 | 1.62 |
| 2 | 17.5 | 4.01 |
| 3.5 | 23.48 | 2.17 |
| 5 | 28.10 | 2.81 |
| 10 | 32.9 | 5.88 |

The color that appeared on the stick is dependent on the presence of LH, and its intensity is proportional to the LH concentration. The plasma without LH (0 ng/ml) does not give any color on the stick, indicating absence of a nonspecific signal.

Figure 3:
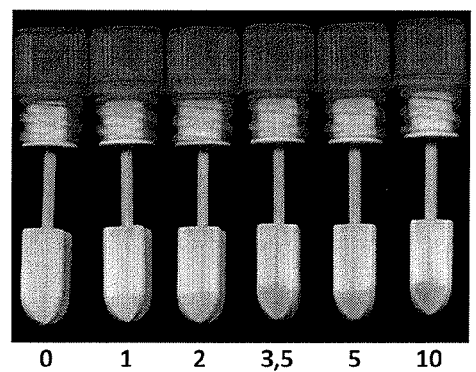
FIG. 3 A shows a photograph of sticks after application of the method of the invention with bovine plasmas comprising different concentrations of LH, namely 0, 1, 2, 3.5, 5 and 10 ng/ml, the sticks having been coated beforehand with PBS buffer solution comprising 20% of fetal calf serum.
Figure 3:
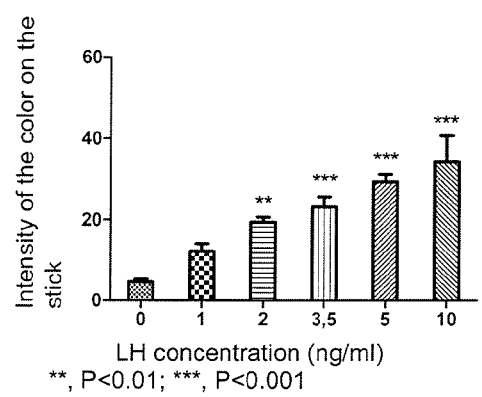

The results shown in FIG. 3 demonstrate that the performance of the stick is greatly improved by using PBS comprising 20 vol % of FCS.

In conclusion, PBS comprising FCS permits quantitative detection of LH as a function of its concentration in a plasma sample.

2. Effect of the Percentage of FCS in PBS

In this example, various percentages of FCS were tested.

The sticks were prepared by the method described in example 1 above. PBS was prepared with the following percentages by volume of FCS: 0, 5, 10, 20, 30, 40 and 50%. Two bovine plasmas were used as samples to be assayed: one at 0 ng/ml and the other at 7 ng/ml in each case. The intensity of the colored signal obtained at 0 and 7 ng/ml of LH was quantified in each case. For each condition, the ratio between the two intensities was calculated; it represents the ratio of the specific signal to the background noise.

Figure 4:
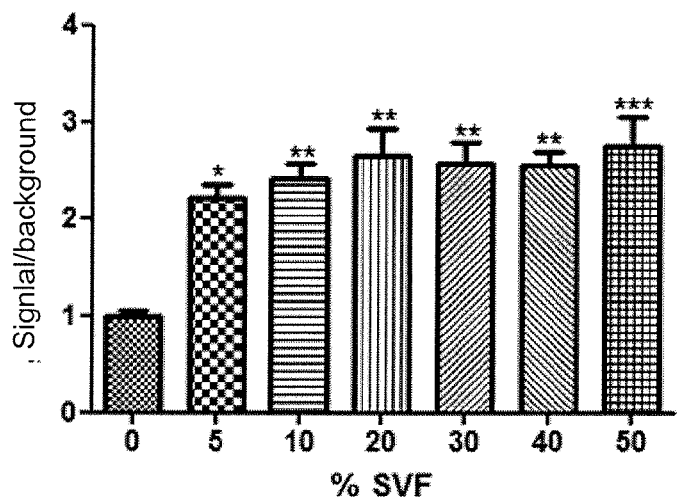
FIG. 4 shows a bar chart presenting the ratio of the intensity of the color of the sticks obtained after application of the method of the invention with a bovine plasma having an LH concentration of 7 ng/ml to that obtained with a bovine plasma having an LH concentration of 0 ng/ml. The sticks having been coated beforehand with PBS buffer solution comprising 0, 5, 10, 20, 30, 40, 50 vol % of fetal calf serum.

The results obtained are presented in FIG. 4, which shows a bar chart of the ratio: color intensity with LH at 7 ng/ml (signal)/color intensity with LH at 0 ng/ml (background noise).

TABLE 4 results of luminous intensity obtained as a function of concentration of FCS

| | Percentage (by volume) of FCS | | | | | | |
|---|---|---|---|---|---|---|---|
| | 0 | 5 | 10 | 20 | 30 | 40 | 50 |
| Intensity with 0 ng/mL of LH | 37.58 ± 4.41 | 13.51 ± 1.03 | 11.25 ± 1.74 | 9.97 ± 1.28 | 9.94 ± 0.15 | 9.41 ± 1.09 | 8.28 ± 0.63 |
| Intensity with 7 ng/mL of LH | 37.17 ± 5.97 | 29.72 ± 3.02 | 26.85 ± 1.28 | 26.32 ± 5.01 | 25.59 ± 3.59 | 23.93 ± 3.06 | 22.55 ± 3.08 |
| Ratio: intensity at 7 ng/ml/intensity at 0 ng/ml | 1.01 | 2.19 | 2.35 | 2.63 | 2.57 | 2.54 | 2.72 |

As demonstrated in FIG. 4 and in Table 4, all the concentrations tested make it possible to obtain a specific signal. In particular, statistical analysis by the method of single-factor analysis of variance followed by a Bonferroni test showed that the percentage of 50 vol % of FCS gives the best ratio of specific signal to background noise with a threshold significant at $p<0.001$. Those obtained with PBS comprising 10 to 40 vol % of FCS are also advantageous and are very significantly different from the conditions with 5% and 0% of FCS (**, $p<0.01$). The condition with 5 vol % of FCS is significantly different from PBS 0 vol % FCS (*, $p<0.05$).

The results obtained show that detection of LH with PBS comprising 20 to 50% of FCS is optimal with a signal/background noise ratio varying from 2.6 to 2.72 respectively. The condition with PBS comprising 50 vol % of FCS is more significant with $p<0.001$. Below the threshold of 20 vol %, the signal obtained with the plasma at 7 ng/ml of LH is higher; however, the nonspecific signal also increases.

This example clearly demonstrates that the method of the invention permits detection of LH as well as visualization of detection.

3. Effect of the Substrate of the Enzyme

In this example, different substrates of peroxidase were evaluated and compared:

Firstly, Membrane TMB versus ELISA TMB, then CN/DAB, DAB, CN, OPD, ODN, AEC versus Membrane TMB from two different suppliers (KPL and Sigma).

a) Effect of different TMBs. The effect of the Membrane TMB marketed by the company KPL (reference 50-77-18) was first compared with that of the Sure Blue TMB (registered trademark) marketed by the company KPL (reference 52-00-00) used for the ELISA techniques.

In this example, the method was carried out on 4 samples of plasmas taken serially from one and the same cow at the time of the preovulatory LH peak, testing each of the developers in parallel. These plasma samples were assayed quantitatively beforehand with the assay kit LH DETECT (registered trademark). Their LH concentrations were 0, 2, 5, 10 ng/ml respectively. This experiment was repeated three times (n=3).

Figure 5:
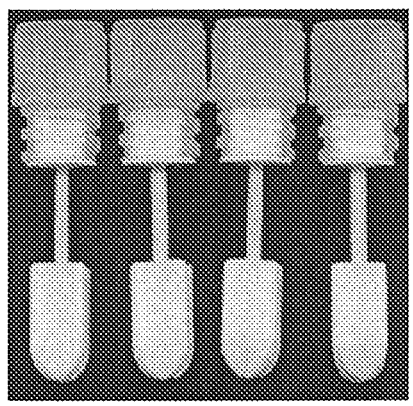
FIG. 5 A shows a photograph of sticks after application of the method of the invention with bovine plasmas comprising different concentrations of LH, namely 0, 1, 2, 5 and 10 ng/ml after detection with Membrane TMB.
Figure 5:
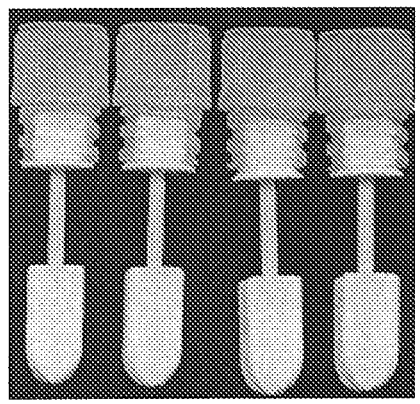
Figure 5:
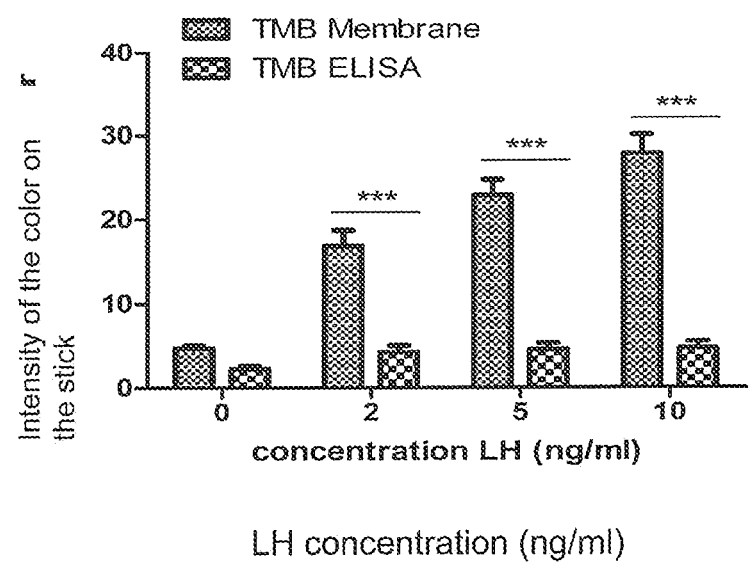

The results obtained are shown in FIG. 5 A to C. FIG. 5 A shows a photograph of sticks obtained after application of the method of the invention with plasmas comprising different concentrations of LH, namely 0, 1, 2, 5 and 10 ng/ml after detection with Membrane TMB. FIG. 5 B shows a photograph of sticks after application of the method of the invention with plasmas comprising different concentrations of LH, namely 0, 1, 2, 5 and 10 ng/ml after detection with ELISA TMB. FIG. 5 C shows a bar chart of the intensity of the color obtained on the sticks in units of density as a function of LH concentration. The bars marked with large-square checker represent the intensity of the color obtained with ELISA TMB. The bars marked with small-square checker represent the intensity of the color obtained with Membrane TMB.

The results shown in FIG. 5 demonstrate very clearly that only the Membrane TMB gives a colored signal on the stick. This colored signal appears at the threshold of 2 ng/ml of LH (FIG. 5A, FIG. 5C). In contrast, no color is observed on the stick detected with ELISA TMB (FIG. 5B and FIG. 5C).

Table 5 below shows the results obtained as a function of the substrates.

TABLE 5 color intensity as a function of LH concentration and of the substrate used.

| LH | Color intensity (mean value ± standard deviation) | |
|---|---|---|
| ng/ml | Membrane TMB | ELISA TMB |
| 0 | 4.76 ± 0.66 | 2.29 ± 0.79 |
| 2 | 16.84 ± 4.21 | 4.25 ± 1.77 |
| 5 | 22.88 ± 4.18 | 4.53 ± 1.74 |
| 10 | 27.81 ± 5.10 | 4.70 ± 1.83 |

As demonstrated in this example, only the sticks detected in Membrane TMB have a very definite blue color, the intensity of which varies in proportion to the concentration up to 10 ng/ml of LH. With the sample without LH, the stick remains white and does not display a nonspecific signal. Advantageously, this property allows very simple visual reading of the test.

Quantification of the color intensity by scanning (Table 5 and FIG. 5C) demonstrated a very significant increase of the signal with Membrane TMB starting from a concentration of 2 ng/ml LH ($p<0.001$). This color is intensified at 5 and 10 ng/ml of LH (Table 5 and FIG. 5C). In contrast, the very low amplitude observed with ELISA TMB is not statistically significant.

As demonstrated in this example, Membrane TMB is therefore an effective developer, giving the best performance both in terms of sensitivity of the test (threshold at 2 ng/ml) and intensity of the color reaction (amplitude of 7 times between the color of the plasma 0 and that of the plasma at 10 ng/ml of LH).

b) Test of other specific substrates of peroxidase: CN/DAB, DAB, CN, OPD relative to Membrane TMB.

In this example, the substrates were CN/DAB (Thermo Scientific, reference 34000), DAB (Thermo Scientific, reference 34002), CN (Sigma, reference C6788) and OPD (Sigma, reference P5412).

The sticks were prepared as described in example 1 above and were incubated in bovine plasma assayed at 19 ng/ml of LH. The contact time in each developer was 15 minutes.

Each stick was incubated in a different developer and then scanned in order to quantify the color intensity obtained. This experiment was repeated three times.

Figure 6:
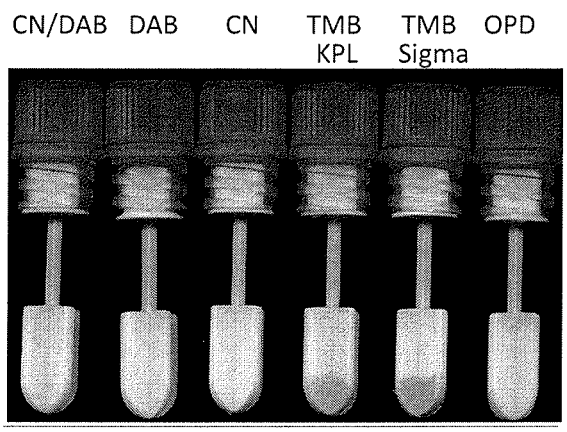
FIG. 6 A shows a photograph of sticks after application of the method of the invention with bovine plasma samples comprising an LH concentration of 19 ng/ml detected with different substrates of the enzyme peroxidase. The substrates used are 3,3'-diaminobenzidine tetrahydrochloride (DAB), 4-chloro-1-naphthol (CN), 4-chloro-1-naphtho/3,3'-diaminobenzidine tetrahydrochloride (CN/DAB), ortho-phenylenediamine (OPD), the Membrane TMB marketed by the company KPL (TMB KPL) or by the company Sigma (TMB Sigma).
Figure 6:
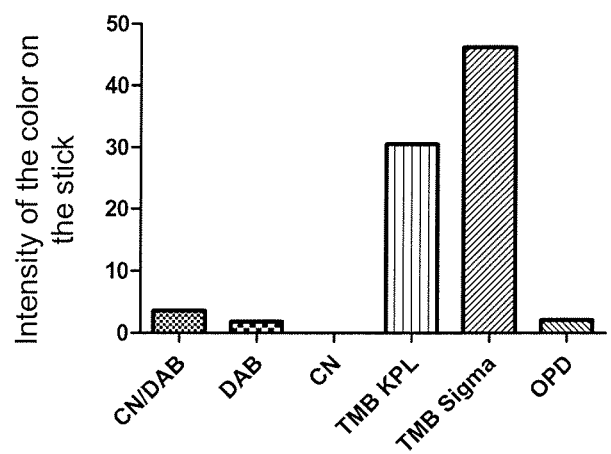

The results are shown in FIG. 6. FIG. 6 A shows a photograph of the sticks detected respectively with 3,3'-diaminobenzidine tetrahydrochloride (DAB), 4-chloro-1-naphthol (CN), 4-chloro-1-naphtho/3,3'-diaminobenzidine tetrahydrochloride (CN/DAB), OPD, the Membrane TMB marketed by the company KPL (TMB KPL) or by the company Sigma (TMB Sigma). FIG. 6 B shows a bar chart of the intensity of the color obtained on the sticks in units of density as a function of the different enzyme substrates indicated above.

As shown in these figures, only the two Membrane TMBs give a significant colored signal, whose value quantified by scanning is from 10 to 20 times greater than that of the other developers used.

This difference is very significant relative to the values obtained with CN/DAB, DAB, CN, OPD ($p<0.001$).

These results all show that Membrane TMB makes it possible to obtain a visual result with a better sensitivity and specificity of the test for detecting the preovulatory LH peak.

c) Test of specific substrates of peroxidase relative to Membrane TMB: CN/DAB, DAB, CN, OPD, ODN and AEC To supplement the comparative study in point b) above, the aforementioned substrates were tested, as well as two other substrates ODN and AEC (Sigma, references D3252 and A6926). This study was carried out with sticks prepared in extreme conditions. Coating was performed with a rabbit anti-bovine LH antibody fixed on the test surface (AC1 at 40 µg/ml), and the peroxidase-coupled horse anti-ovine LH antibody (AC2 HRP) was also prepared at a concentration of 40 µg/ml. A bovine plasma at 19 µg/ml was used. The experiment was repeated three times.

Figure 7:
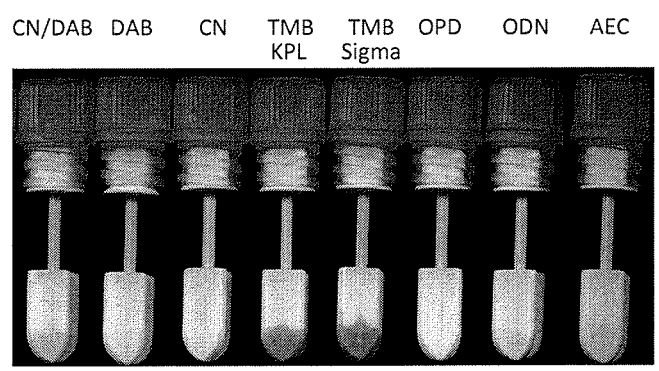
FIG. 7 A shows a photograph of sticks after application of the method of the invention with bovine plasma samples comprising an LH concentration of 19 ng/ml detected with different substrates of the enzyme. The substrates used are 3,3'-diaminobenzidine tetrahydrochloride (DAB), 4-chloro-1-naphthol (CN), 4-chloro-1-naphtho/3,3'-diaminobenzidine tetrahydrochloride (CN/DAB), ortho-phenylenediamine (OPD), 3,3-dimethoxybenzidine-o-dianisidine (ODN), 3-amino-9-ethylcarbazole (AEC), the Membrane TMB marketed by the company KPL (TMB KPL) or by the company Sigma (TMB Sigma).
Figure 7:
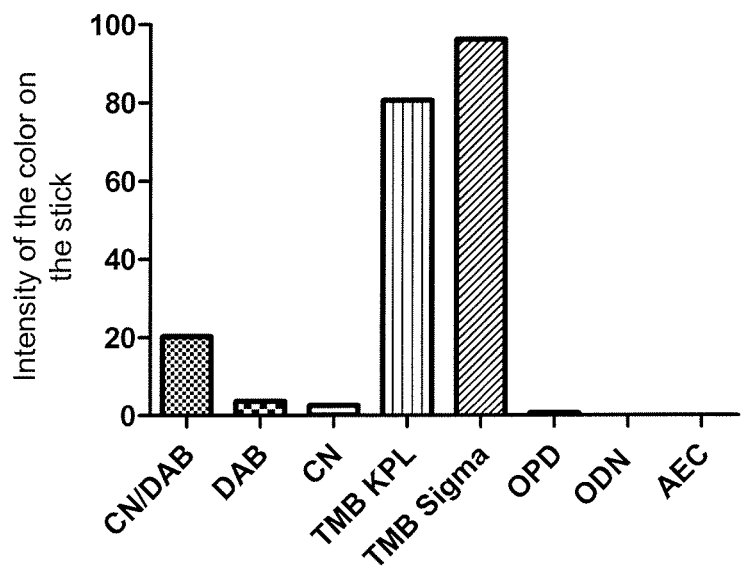

The results are shown in FIGS. 7 A and B. FIG. 7 A shows a photograph of sticks after application of the method of the invention with bovine plasma samples comprising an LH concentration of 19 ng/ml detected with different substrates of the enzyme. The substrates used are 3,3'-diaminobenzidine tetrahydrochloride (DAB), 4-chloro-1-naphthol (CN), 4-chloro-1-naphtho/3,3'-diaminobenzidine tetrahydrochloride (CN/DAB), OPD (ortho-phenylenediamine), OND (3,3-dimethoxybenzidine-o-dianisidine), AEC (3-amino-9-ethyl-carbazole), the Membrane TMB marketed by the company KPL (TMB KPL) or by the company Sigma (TMB Sigma).

FIG. 7 B shows a bar chart of the intensity of the color obtained on the sticks in units of density as a function of the different substrates of the enzyme: 3,3'-diaminobenzidine tetrahydrochloride (DAB), 4-chloro-1-naphthol (CN), 4-chloro-1-naphtho/3,3'-diaminobenzidine tetrahydrochloride (CN/DAB), OPD (ortho-phenylenediamine), OND (3,3-dimethoxybenzidine-o-dianisidine), AEC (3-amino-9-ethyl-carbazole), the Membrane TMB marketed by the company KPL (TMB KPL) or by the company Sigma (TMB Sigma).

TABLE 7 intensity values obtained as a function of the substrate

| Substrate | CN/DAB | DAB | CN | TMB | TMB Sigma | OPD | ODN | AEC |
|---|---|---|---|---|---|---|---|---|
| Intensity | 20.3 | 3.7 | 2.6 | 80.6 | 96.1 | 0 | 2.6 | 4.0 |

As shown in FIGS. 7 A and B and in Table 7 above, the two Membrane TMBs allow a very high colored signal to be obtained, i.e. between 80 and 90 units, four times greater than the signal obtained with CN/DAB: 20 units, the latter being very difficult to detect visually. DAB, CN and OPD do not give a signal visible to the eye, i.e. between 0 and 3.7 units, the stick remains white after development. ODN and AEC give a slight pink coloration that is detectable visually, but it disappears in a few minutes. For this reason, quantification is impossible.

These results all show that the substrates CN/DAB, DAB, CN, OPD, ODN and AEC are not developers suitable for use of the stick. Even in extreme conditions of preparation of the sticks, using very high concentrations of AC1 and of AC2 HRP (40 µg/ml), these developers only develop a zero or very low signal relative to Membrane TMB. Moreover, these high concentrations of anti-LH antibody fixed on the surface (AC1) and of anti-LH antibody coupled to peroxidase (AC2 HRP) introduce a high nonspecific signal, which greatly reduces the sensitivity and specificity of detection.

In conclusion, compared with other substrates, Membrane TMB gives the best ratio of specific signal to nonspecific signal. The intensity of the color reaction on the stick and the absence of background noise make it the most advantageous developer, regardless of the supplier of the product. This optimal sensitivity makes it possible to detect visually, unambiguously, the presence of LH in the sample to be assayed from the appearance of a blue signal without any nonspecific interference.

4. Effect of the Conditions of Preparation of Membrane TMB

The inventors investigated the benefit of diluting the Membrane TMB in different buffers for maximum reduction of the background noise without lowering the intensity of the colored signal.

For this, three parameters were investigated:
a) the dilution of Membrane TMB in different buffers,
b) the dilution factor of the Membrane TMB in a citrate buffer, and
c) the molarity of the citrate buffer used.

In each series, the results were compared with those obtained with pure Membrane TMB. The sticks were prepared in the conditions of manufacture described in example 1 above.

a) Preparation of Membrane TMB in Different Buffers

To evaluate the effect of the composition of the buffer for diluting the Membrane TMB, three buffers were used in parallel for diluting it to 50%:

PBS ($K_2HPO_4/KH_2PO_4$ 0.01 M-NaCl 0.15M) pH 7.4 (marketed by VWR, references 26930.293, 26936.293, 27810.295), citrate buffer ($NaCH_3CO_2/CH_3COOH$) 0.03M pH5 (marketed by VWR, reference 27652.298 and Carlo Erba Reagents, reference 302 002), and phosphate buffer 0.01M ($K_2HPO_4/KH_2PO_4$) pH 7.4 (marketed by VWR, references 26930.293, 26936.293).

Two samples of plasmas from Holstein cows were used: one at 0 ng/ml to evaluate the effect on the background noise and the other at 5 ng/ml of LH to evaluate the effect on the intensity of the colored signal, these two parameters determining the sensitivity of the test. The results are shown in FIG. 8 and in Table 8 below.

Figure 8:
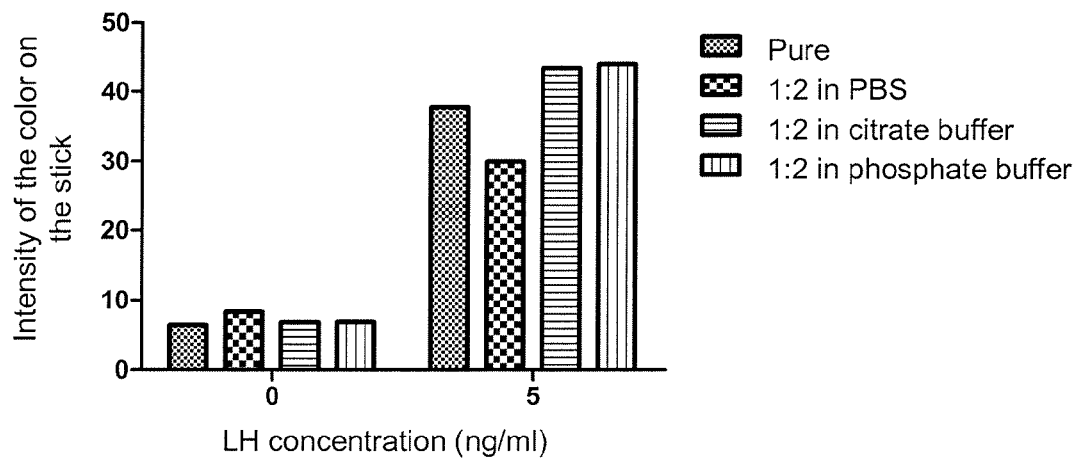
FIG. 8 shows a bar chart of the intensity of the color obtained on the sticks in units of density as a function of the LH concentration in the plasmas: 0 or 5 ng/ml and as a function of the dilution to 50 vol % of the Membrane TMB in PBS ($K_2HPO_4/KH_2PO_4$ 0.01 M-NaCl 0.15M) pH 7.4 (bars with large squares); in citrate buffer ($NaCH_3CO_2/CH_3COOH$) 0.03M pH5 (bars hatched horizontally); in phosphate buffer 0.01M ($K_2HPO_4/KH_2PO_4$) pH 7.4 (bars hatched vertically), or Membrane TMB without dilution (pure) (bars with small squares).

FIG. 8 shows a bar chart of the intensity of the color obtained on the sticks in units of density as a function of the LH concentration: 0 or 5 ng/ml and as a function of dilution to 50% of Membrane TMB in PBS ($K_2HPO_4/KH_2PO_4$ 0.01 M-NaCl 0.15M) pH 7.4 (bars with large squares); a citrate buffer ($NaCH_3CO_2/CH_3COOH$) 0.03M pH5 (bars hatched horizontally); phosphate buffer 0.01M ($K_2HPO_4/KH_2PO_4$) pH 7.4 (bars hatched vertically).

TABLE 8 intensity of detection as a function of the LH concentration
and as a function of the buffer for diluting the Membrane TMB

| Buffer | Pure | ½ PBS | ½ citrate buffer | ½ phosphate buffer |
|---|---|---|---|---|
| Signal intensity with 0 ng/ml of LH | 6.42 | 8.35 | 6.85 | 6.95 |
| Signal intensity with 5 ng/ml of LH | 37.77 | 29.98 | 43.45 | 44.5 |

A statistical analysis of the color intensities of the stick obtained was performed with the Bonferroni test.

The intensities of the colored signal obtained with TMB diluted in the three dilution buffers are not significantly different for the plasma at 0 ng/ml of LH. The dilution buffer therefore does not have a significant influence on the nonspecific signal.

With the 5 ng/ml plasma, the intensities of the colored signal vary depending on the dilution buffer used, but these differences are not significant. Nevertheless, TMB diluted to 50% in PBS gives a weaker colored signal (29.98) compared to the citrate buffer (43.45) and the phosphate buffer (44.5), which give a more intense colored signal. The inventors noted that there is no significant difference between the citrate and phosphate buffers: the intensities of the colored signal obtained in both cases are almost equal, with a slightly higher value in the case of dilution with citrate buffer.

The results and the statistical analysis have shown that with plasma at 0 ng/ml, the color intensities of the stick obtained are not statistically different from one another.

However, the inventors demonstrated, surprisingly, that preparation of Membrane TMB in 50% of citrate buffer 0.03M pH 4.5 gives the best performance of the stick with a very low zero signal and a higher signal at 5 ng/ml (better specific signal/background noise ratio). Advantageously, this makes it possible to detect the LH peak with high sensitivity and high specificity and advantageously gives better visual detection.

b) the Dilution Factor of Membrane TMB in Citrate Buffer

Different dilutions of Membrane TMB in 0.03M citrate buffer were also evaluated in order to optimize the composition of the developer and minimize the risks of a nonspecific signal in the presence of very low concentrations of LH. The Membrane TMB was diluted by half each time down to ¹⁄₁₆ using sticks prepared according to the standard production conditions, i.e. by the method described in example 1 above. A plasma from a Holstein cow at 7.2 ng/ml of LH was used as the sample.

Figure 9:
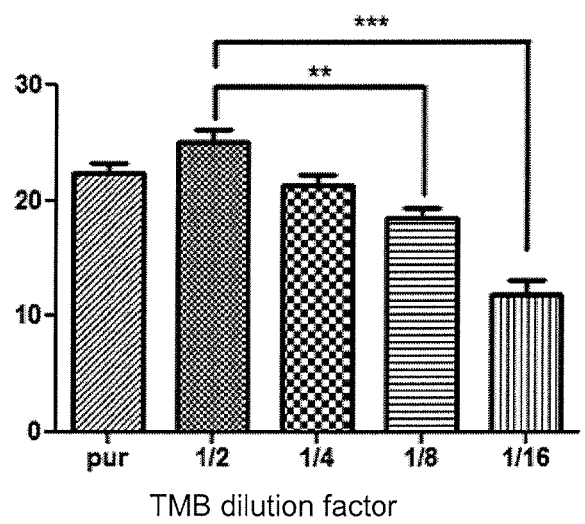
FIG. 9 shows a bar chart of the intensity of the color obtained on the sticks in units of density as a function of dilution to ½, ¼, ⅛ and 1/16 of Membrane TMB in citrate buffer ($NaCH_3CO_2/CH_3COOH$) 0.03M pH5, or Membrane TMB without dilution (pure).

The results obtained are shown in FIG. 9 and in Table 9 below.

FIG. 9 shows a bar chart of the intensity of the color obtained on the sticks in units of density as a function of dilution to ½, ¼, ⅛ and ¹⁄₁₆ Membrane TMB in citrate buffer ($NaCH_3CO_2/CH_3COOH$) 0.03M pH5, or without dilution (pure).

Each experiment was carried out four times. Statistical analysis of the results was performed by analysis of variance followed by a Bonferroni test.

TABLE 9 results of color intensity as a function of the dilution of the citrate buffer

| Dilution | Pure | ½ | ¼ | ⅛ | ¹⁄₁₆ |
|---|---|---|---|---|---|
| Mean ± SEM | 22.27 ± 1.68$^a$ | 25.01 ± 1.87$^{a,b}$ | 21.39 ± 1.38$^a$ | 18.53 ± 1.48$^c$ | 11.93 ± 1.95 |

In the table,
$^a$corresponds to $p < 0.001$ if compared with dilution to ¹⁄₁₆,
$^b$corresponds to $p < 0.01$ if compared with dilution to ⅛ and
$^c$corresponds to $p < 0.01$ if compared with dilution to ¹⁄₁₆.

The results obtained showed, surprisingly, that TMB diluted to ½ in 0.03M citrate buffer gives a stronger colored signal than that obtained with pure TMB or diluted to ¼. However, these differences are not significant. Starting from dilution to ¼, the decrease in the signal is greater and results in a value of 11.93 units at ¹⁄₁₆ dilution. Statistical analysis shows that only the Membrane TMB diluted to ½ is significantly different from that diluted to ⅛ and ¹⁄₁₆.

Consequently, and surprisingly, the inventors have demonstrated that dilution of Membrane TMB to half in citrate buffer makes it possible to obtain a stronger intensity of the colored signal in the presence of LH and a very low intensity of nonspecific colored signal (background noise), i.e. below 5 units of density, a value that is no longer detectable visually.

Dilution therefore makes it possible, advantageously, to increase the detection sensitivity of the method while permitting better visual detection.

c) Effect of the Molarity of the Citrate Buffer Used for Diluting the Membrane TMB The concentration of the citrate buffer was also investigated. The concentrations tested were 0.003M, 0.03M, 0.3M and 3M. The sticks used were prepared in the standard production conditions, i.e. by the method described in example 1 above. A plasma from a Holstein cow at 27 ng/ml of LH was used as the sample.

Figure 10:
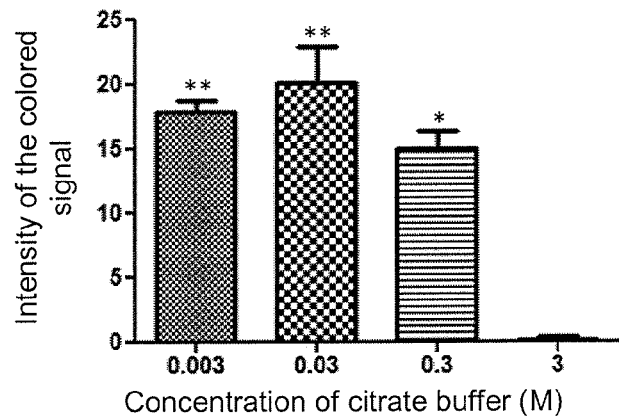
FIG. 10 shows a bar chart of the intensity of the color obtained on the sticks in units of density with a bovine plasma with LH concentration of 27 ng/ml, as a function of the molar concentration of the citrate buffer.

In this example, the Membrane TMB was diluted to ½ with the various citrate buffer solutions mentioned above. The results are presented in FIG. 10 and in Table 10 below. FIG. 10 shows a bar chart of the intensity of the color obtained on the sticks in units of density as a function of the molar concentration of the citrate buffer.

TABLE 10 results of color intensity obtained as a function
of the molar concentration of the citrate buffer

| Molarity | 0.003M | 0.03M | 0.3M | 3M |
|---|---|---|---|---|
| Signal intensity | 17.9 ± 1.3** | 20.1 ± 4** | 15.1 ± 1.9* | 0.2 ± 0.3 |

The results were analyzed statistically by analysis of variance followed by a Bonferroni test. This study showed that the colored signals of the sticks obtained at molarities of 0.003M, 0.03M and 0.3M are not statistically different from one another. In contrast, these three molarities are significantly different from the result obtained with a 3M citrate buffer, which extinguishes any colored signal.

Thus, the inventors showed, surprisingly, that the molarity of the citrate buffer has an effect on development of the LH peak. In particular, the inventors showed, surprisingly, that a molarity of 0.03M of the citrate buffer advantageously makes it possible to obtain a strong coloration, permitting visual detection.

5 Comparison of the Effect of FCS in PBS Buffer Relative to Other Protein Components The effect of adding 50 vol % of FCS to PBS ($K_2HPO_4$/ $KH_2PO_4$ 0.01 M-NaCl 0.15M) pH 7.4) was compared with that of other proteins or serum.

For this, the following 4 solutions were tested:
PBS comprising 50 vol % FCS,
PBS comprising 3% casein (30 g/L),
PBS comprising 4% BSA (40 g/L), and
PBS comprising 5% skim milk (50 g/L).

The experiment was repeated three times.

FCS is the FCS marketed by Lonza under the reference 14-801 F, casein marketed by Sigma under the reference C8654, bovine serum albumin (BSA) marketed by PAA under the reference K45012, skim milk marketed by Régilait.

Figure 11:
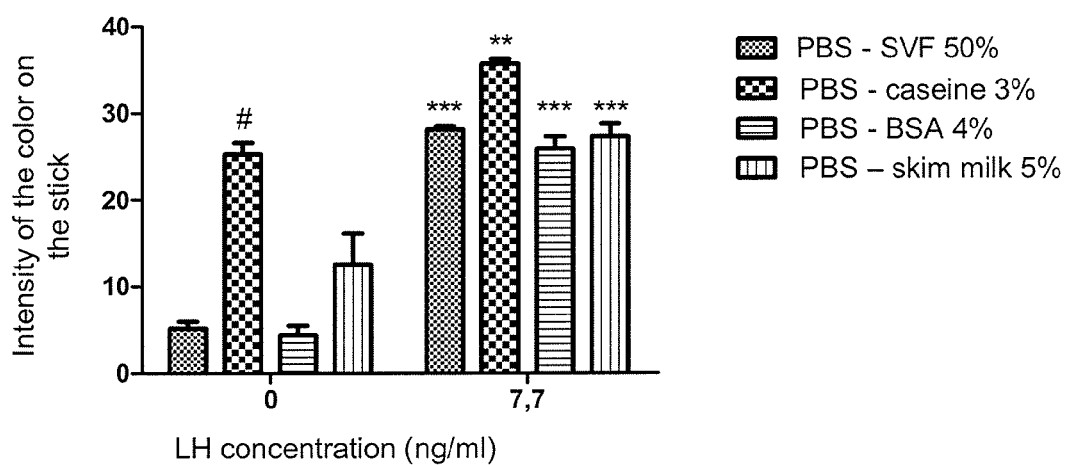
FIG. 11 shows a bar chart of the intensity of the color obtained on the sticks in units of density as a function of the LH concentration: 0 or 7.7 ng/ml and as a function of the protein medium present in the phosphate-buffered saline, namely fetal calf serum at 50 vol % (bars with small squares), casein at 3% (30 g/L) (bars filled with large squares), bovine serum albumin (BSA) at 4% (40 g/L) (bars hatched horizontally), or skim milk at 5% (50 g/L) (bars with horizontal hatching).

The test surfaces were prepared by the method described in example 1. Two plasmas from Holstein cows were used as the sample: one at 0 ng/ml and the other at 7.7 ng/ml. The intensity of the colored signal obtained was quantified in each case by the method described above. The results are shown in FIG. 11 and in Table 11 below. FIG. 11 shows a bar chart of the intensity of the color obtained on the sticks in units of density as a function of the LH concentration: 0 or 7.7 ng/ml and as a function of the protein component present in the phosphate-buffered saline, namely fetal calf serum at 50 vol % (bars with small squares), casein at 3% (30 g/L) (bars filled with large squares), bovine serum albumin (BSA) at 4% (40 g/L) (bars hatched horizontally), or skim milk at 5% (50 g/L) (bars with horizontal hatching).

TABLE 11 results for the color intensity obtained as a function of the protein component

| | PBS comprising by volume | | | |
|---|---|---|---|---|
| | FCS 50% | Casein 3% | BSA 4% | Skim milk 5% |
| Signal at 0 ng/ml LH | 5.16 ± 0.8 | 25.22 ± 1.36 | 4.39 ± 1.09 | 12.51 ± 3.64 |
| Signal at 7.7 ng/ml LH | 28.11 ± 0.41 | 35.65 ± 0.49 | 20.89 ± 1.38 | 27.29 ± 1.49 |
| Ratio signal/ background noise | 5.45 | 1.41 | 4.75 | 2.18 |

As demonstrated in FIG. 11 and in Table 11 above, with PBS comprising 50 vol % of FCS or 4% (40 g/L) of BSA, a very slight, nonvisible coloration is obtained with the plasma at 0 ng/ml of LH, demonstrating advantageously absence of a nonspecific signal.

In contrast, stronger coloration of the surface, detectable visually, is obtained with PBS comprising 5% (50 g/L) of skim milk (12.51), showing a disadvantageous nonspecific signal. PBS comprising 3% (30 g/L) of casein is even less favorable, giving a very high nonspecific signal (25.22).

In all cases, the values obtained with the plasma with 7.7 ng/ml of LH are significantly different from the intensity obtained with the plasma with 0 ng/ml of LH: for the buffers PBS-FCS 50 vol %, PBS-BSA 4% (40 g/L) and PBS-milk 5% (50 g/L) (*, $p<0.001$) and for PBS-casein 3% (30 g/L) (, $p<0.01$).

The effect of the different media was found by calculating the ratio of signal (at 7.7 ng/ml) to background noise (at 0 ng/ml). This ratio varies depending on the buffer used, it is the most favorable with PBS-FCS 50 vol % (5.45) and the least favorable with PBS-casein 3% (30 g/L) (1.41).

In conclusion, these results demonstrate the importance of the protein components added to the buffer for coating the test surface and for preparing the enzyme-coupled anti-LH antibody, in this example the peroxidase-coupled anti-LH antibody (AC2 HRP).

As demonstrated in this example, stick performance in fact varies considerably, depending on the buffer used. The best result is obtained with PBS comprising FCS, in particular 50 vol % of FCS.

6 Comparative Tests with Different Enzymes

Other coupling enzymes were tested to evaluate their functionality in the method of the invention and the kit as manufactured by the method described in example 5.

Thus, three enzymes were compared with peroxidase:
glucose oxidase,
beta-galactosidase, and
alkaline phosphatase.

The glucose oxidase used was the glucose oxidase marketed by Sigma Aldrich derived from *Aspergillus niger* under the catalog reference Ref: G7141 in the form of powder. The powder was weighed and resuspended at 1 mg/ml in 1 ml of 0.1M carbonate-bicarbonate buffer ($NaHCO_3$/$Na_2CO_3$ 0.1 M pH 9.6) (marketed respectively by Prolabo under the reference 27778.293 and by VWR under the reference 27771.290).

Coating of the test surface (contacting) of the fins of the stick was carried out directly by incubating it in the solution at 1 mg/ml for one hour at 37° C., then for one hour at 4° C. The sticks were washed for 10 seconds in a vessel containing PBS ($K_2HPO_4$/$KH_2PO_4$ 0.01 M-NaCl 0.15M) pH 7, (VWR, ref. 26930.293, 26936.293, 27810.295) and immersed for 15 minutes in the substrate solution comprising:
7.5 g D-glucose,
0.1 g PMS (phenazine methosulfate), and
0.5 g NBT (Nitro-Blue-tetrazolium),
dissolved in 1 liter of 0.1 M $Na_2HPO_4$ buffer pH 6.9.

Figure 12:
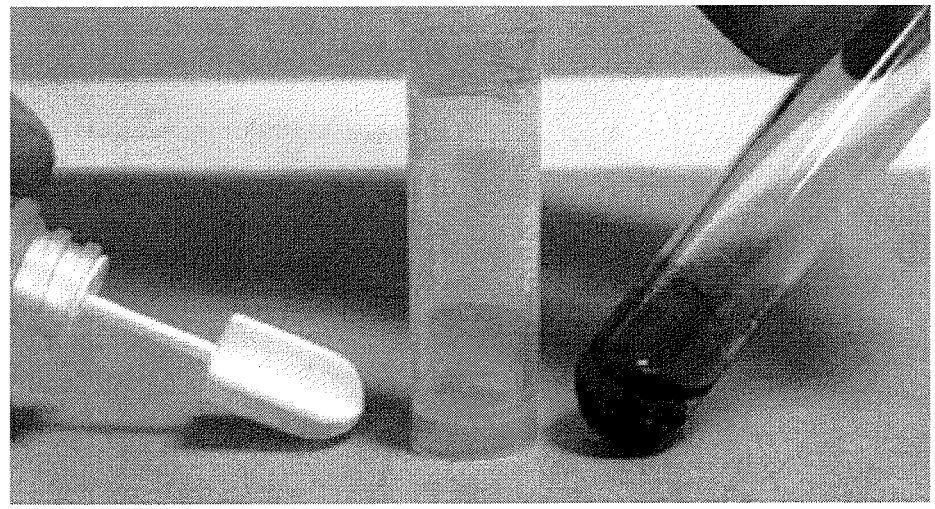
FIG. 12 A shows a test surface (fins of the stick) sensitized according to the application of the method with glucose oxidase and immersed in its substrate (PMS/NBT), FIG. 12 B shows the substrate solution in which the test surface was immersed, FIG. 12 C shows a photograph of a tube in which glucose oxidase in solution was brought into contact with its substrate.

FIG. 12 A shows the photograph of the test surface (fins of the stick) obtained after development and shows that color does not appear on the stick, which remains white, or in the substrate solution (FIG. 12 B).

A positive control was conducted by adding 25 µl of glucose oxidase at 1 mg/ml to 250 µl of substrate; in this case, a deep blue precipitate appears instantaneously. These results demonstrate that glucose oxidase is active in solution (FIG. 12 C) but does not react with its substrate when it is adsorbed on the surface of the stick (FIG. 12 C).

The beta-galactosidase used, derived from *Escherichia coli*, is marketed by Sigma Aldrich under the catalog reference Ref: G5635 in the form of powder. It was prepared at 1 mg/ml in 1 ml of carbonate-bicarbonate buffer ($NaHCO_3$/ $Na_2CO_3$ 0.1 M pH 9.6) (powders marketed respectively by Prolabo under the reference 27778.293 and by VWR under the reference 27771.290).

Coating of the test surface (contacting) of the fins of the stick was performed by incubation with a 50 μg/ml solution for one hour at 37° C., then for one hour at 4° C.

The sticks were washed for 10 seconds in a vessel containing PBS (K$_2$HPO$_4$/KH$_2$PO$_4$ 0.01 M-NaCl 0.15M, pH 7.4) (powders marketed by VWR, ref. 26930.293, 26936.293, 27810.295) and immersed for 18 hours at 37° C. in the substrate solution comprising: X-Gal (marketed by the company Uptima/Interchim in the form of powder, catalog reference Ref: UP40534M) diluted at 4 mg/ml in 1 ml of DMSO (Sigma, ref D8418) then at 1 mg/ml in 1 ml of PBS (K$_2$HPO$_4$/KH$_2$PO$_4$ 0.01 M-NaCl 0.15M, pH 7.4). Another preparation of X-Gal substrate was also tested: a stock solution prepared at 40 mg/ml in 1 ml of DMSO (Sigma, ref D8418) was diluted to 1 mg/ml in 1 ml of PBS (K$_2$HPO$_4$/KH$_2$PO$_4$ 0.01 M-NaCl 0.15M, pH 7.4) (powders marketed by VWR, references 26930.293, 26936.293, 27810.295 with addition of 3 mM potassium ferrocyanide (1.27 g/l), 3 mM potassium ferricyanide (0.99 g/l) (Sigma, ref. HT201 and 702587).

Figure 13:
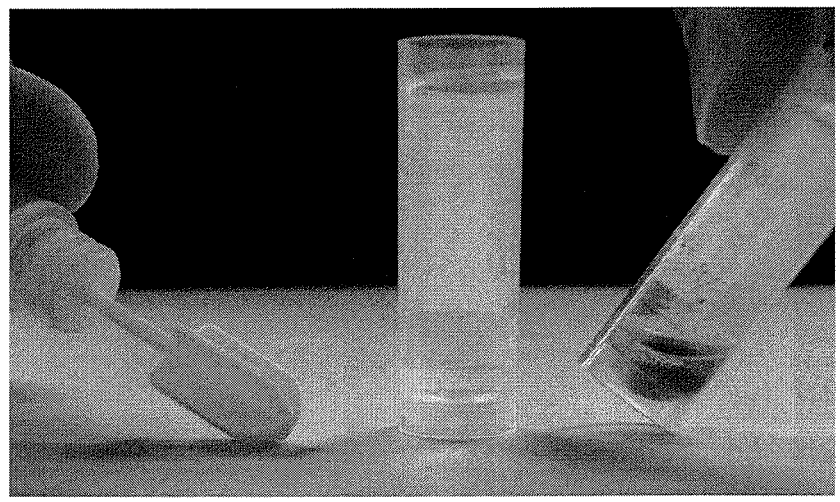
FIG. 13 A is a photograph of a test surface (fins of the stick) on application of the method with beta-galactosidase and immersed in its substrate (X-gal), FIG. 13 B shows the substrate solution in which the test surface was immersed, FIG. 13 C shows a photograph of a tube in which beta-galactosidase in solution was brought into contact with its substrate.

The results showed that in both cases, no color appears on the stick (test surface), which remained white (FIG. 13 A), or in the substrate that had been in contact with the stick for 18 hours at 37° C. (FIG. 13 B).

A positive control, conducted by adding 12.5 μl of beta-galactosidase at 1 mg/ml to 250 μl of substrate, gives a deep blue precipitate, which appears instantaneously (FIG. 13C).

These results demonstrate that beta-galactosidase is active in solution but does not react with its substrate when it is adsorbed on the surface of the stick.

The alkaline phosphatase used is marketed by Sigma Aldrich under the catalog reference P0114, in liquid form at 19 mg/ml. This solution was adsorbed on the test surface, fins of the stick, at a concentration of 50 μg/ml by incubating for one hour at 37° C. and then for one hour at 4° C.

The sticks were washed for 10 seconds in PBS (K$_2$HPO$_4$/KH$_2$PO$_4$ 0.01 M-NaCl 0.15M, pH 7.4) (powders marketed by VWR, ref. 26930.293, 26936.293, 27810.295) and immersed for 30 minutes in a BCIP/NBT substrate solution marketed by the company Uptima/Interchim under the catalog reference UP09985.

Figure 14:
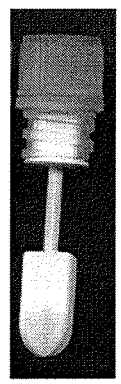
FIG. 14 is a photograph showing a stick test surface (fins of the stick) obtained on application of the method with alkaline phosphatase.

The results presented in FIG. 14 show that a blue color appears on the stick in this case, demonstrating that alkaline phosphatase adsorbed directly on the stick reacts with its substrate and develops a colored signal.

A second experiment was carried out with sticks, the fins of which were contacted and on which polyclonal anti-bovine LH antibody produced in the rabbit at 20 μg/ml was fixed. The antibody was produced by the supplier Eurogentec (Belgium) by its method "Standard antiprotein packages 28-day Speedy in Rabbit" (brand name), then the fins (test surface) were contacted and coated with a solution of PBS (K$_2$HPO$_4$/KH$_2$PO$_4$ 0.01 M-NaCl 0.15M, pH 7.4) (powders marketed by VWR, ref. 26930.293, 26936.293, 27810.295) comprising 50% (by volume) of FCS (fetal calf serum marketed by Lonza, reference 14-801F) according to the manufacturing protocol described in example 1. After incubation for 15 minutes in a plasma from a Holstein cow assayed at 7 ng/ml of LH or in a solution without LH (0 ng/ml), the sticks were incubated for 15 minutes in a solution of noncoupled anti-LH antibody (non-coupled AC2), namely polyclonal anti-LH antibodies produced in the horse by the method described in example 1 prepared at 10 μg/ml in 500 μl of PBS-FCS at 50% (by volume) (see composition above). After washing in 50 ml of PBS (K$_2$HPO$_4$/KH$_2$PO$_4$ 0.01 M-NaCl 0.15M, pH 7.4), the sticks were dried and then incubated for 15 minutes:

either in a solution of polyclonal anti-horse IgG antibody, produced in the rabbit and conjugated to alkaline phosphatase (AC3-PA), marketed by the company Jackson Laboratories under the reference 308-035-003, and prepared at 1/1250th in PBS-FCS at 50% (by volume) (see composition above). After washing in 50 ml of PBS (K$_2$HPO$_4$/KH$_2$PO$_4$ 0.01 M-NaCl 0.15M, pH 7.4), the sticks were developed in a BCIP/NBT substrate solution marketed by the company Uptima/Interchim under the catalog reference UP09985.

or in a solution of polyclonal anti-horse IgG antibody, produced in the rabbit and conjugated to peroxidase (AC3-HRP), marketed by the company Jackson Laboratories under the reference 308-035-003, and prepared at 1/1250th in PBS-FCS at 50% (by volume) (see composition above). After washing in 50 ml of PBS (K$_2$HPO$_4$/KH$_2$PO$_4$ 0.01 M-NaCl 0.15M, pH 7.4), the sticks were developed in a Membrane TMB substrate solution marketed by the company KPL.

Figure 15:
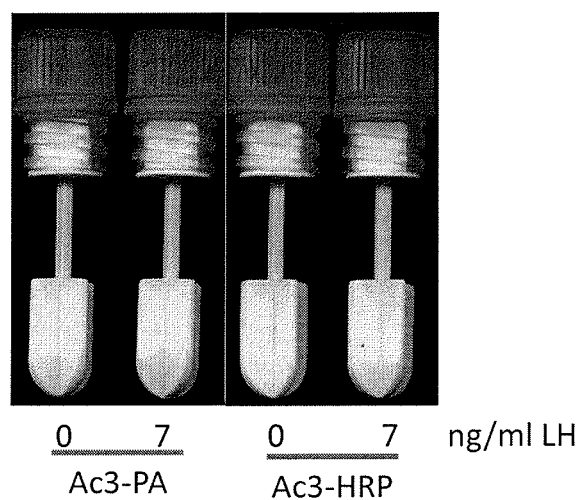
FIG. 15 shows a photograph of sticks after application of the method of the invention with samples of bovine plasmas comprising an LH concentration of 0 or 7 ng/ml (marked "0" and "7") as a function of the enzyme coupled to an anti-horse IgG antibody (AC3) namely alkaline phosphatase (Ac3-PA) or peroxidase (Ac3-HRP). In this case, the horse anti-LH antibody (AC2) is not enzyme-coupled.

FIG. 15 is a photograph showing the results obtained with the two series of sticks and shows that the signal obtained with AC3 conjugated to alkaline phosphatase (Ac3-PA) is very weak (FIG. 15, Ac3PA, 7 ng/ml LH) but with a high nonspecific signal (FIG. 15, Ac3PA, 0 ng/ml LH). In contrast, the colored signal obtained with AC3 conjugated to peroxidase (FIG. 15, Ac3HRP, 7 ng/ml LH) is twice as intense and no background noise is observed (FIG. 15, Ac3PA, 0 ng/ml LH).

The intensity values obtained are given in Table 12 below.

TABLE 12

| intensity of the coloration obtained as a function of the coupled enzyme | | | |
| --- | --- | --- | --- |
| Alkaline phosphatase | | Peroxidase | |
| Plasma 0 ng/ml LH | Plasma 7 ng/ml LH | Plasma 0 ng/ml LH | Plasma 7 ng/ml LH |
| 4.31 | 8.15 | 0.8 | 16.6 |

This example clearly demonstrates that peroxidase is the enzyme that is the most functional, most effective and most suitable for application of the method of detecting the LH peak, with high sensitivity and easy visual reading, and can be interpreted unambiguously.

f) Comparative Tests with Different Anti-LH Antibodies

The method and the kit as described in examples 1 and 5 were employed, using either one different anti-LH antibody (AC1 or AC2) or using two different anti-LH antibodies (AC1 and AC2).

Three conditions were evaluated:

antibody fixed on the test surface (AC1) identical to that of example 1 and different enzyme-coupled antibody (AC2 HRP), antibody fixed on the test surface different and enzyme-coupled antibody identical to that of example 1, and antibody fixed on the test surface and enzyme-coupled antibody, both different relative to example 1.

In the first case, all the sticks (test surface) were coated with the antibody used in example 1, namely the polyclonal anti-bovine LH antibody produced in the rabbit, prepared at 20 μg/ml. Four Holstein cow plasmas at 0, 1, 3.5 and 5 ng/ml of LH respectively were used as samples. The experiment was repeated 3 times.

Two peroxidase-coupled antibodies were tested: the polyclonal antibody used in example 1, namely the polyclonal anti-ovine LH antibody produced in the horse (AC2 HRP), which is the antibody in example 1, and a polyclonal anti-porcine LH antibody produced in the rabbit (AC2 HRP new), which is the antibody produced, for example, by immunization of rabbits by the method described for example in the reference "Radio-immunoassay of the plasma luteinizing hormone in the sheep. Development of the assay technique", Pelletier J., Kann G., Dolais J., Rosselin G., *C. R. Acad. Sc. Paris,* 1968 June; 266: 2291-2294 [5]. It was the method comprising for example three injections of 200 µg of purified porcine LH marketed by the company Tucker Endocrine Research Institute LLC TUENRE (Atlanta, USA), which were performed every two weeks, followed by ten boosters with 100 µg of purified porcine LH carried out every five weeks. Blood samples were taken six and nine days after each booster and 40 ml of blood was obtained. From the blood samples, the rabbit antibodies were purified by affinity chromatography on Protein A Sepharose gel according to the method described in "Techniques Immuno-enzymatiques" Thérèse Ternynck and Stratis Avrameas, éditions INSERM, 1987 [1]. Coupling of the antibody was performed by the method described in "Techniques Immuno-enzymatiques" Thérèse Ternynck and Stratis Avrameas, éditions INSERM, 1987 [1]. The two peroxidase-coupled antibodies were prepared at a concentration of 10 µg/ml in PBS-FCS at 50% (by volume) ($K_2HPO_4/KH_2PO_4$ 0.01 M-NaCl 0.15M, pH 7.4) (powders marketed by VWR, ref. 26930.293, 26936.293, 27810.295) comprising 50% (by volume) of FCS (fetal calf serum marketed by Lonza, reference 14-801F). The developer used was Membrane TMB marketed by KPL under the reference 50-77-18 diluted to half in citrate buffer ($NaCH_3CO_2/CH_3COOH$ 0.03M, pH 5, powders marketed by VWR, reference 27652.298 and Carlo Erba Reagents, reference 302 002).

Figure 16:
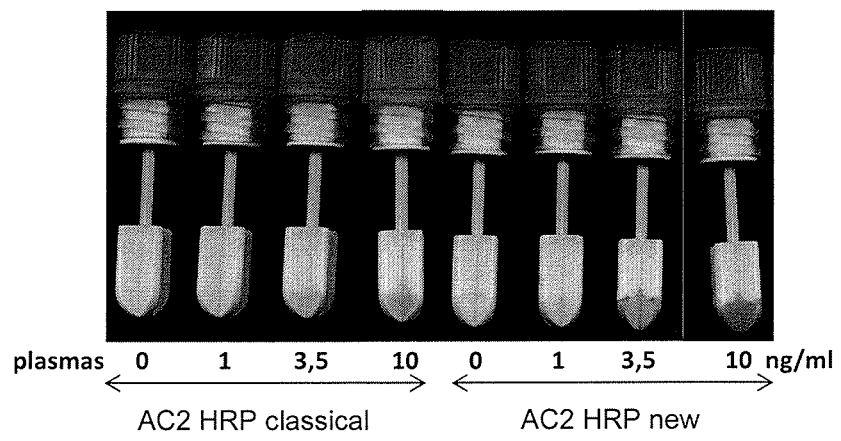
FIG. 16 shows a photograph of sticks after application of the method of the invention with samples of bovine plasmas comprising an LH concentration of 0, 1, 3.5 and 10 ng/ml as a function of the antibody coupled to the peroxidase (denoted HRP) namely an anti-ovine LH antibody produced in the horse indicated AC2 HRP conventional or an anti-porcine LH antibody produced in the rabbit indicated AC2 HRP new.

The results obtained are presented in FIG. 16 and Table 13 below. FIG. 16 shows a photograph of sticks after application of the method of the invention with samples of cow plasmas comprising an LH concentration of 0, 1, 3.5 and 10 ng/ml as a function of the antibody coupled to the peroxidase, namely the coupled antibody identical to that of example 1 (AC2 HRP) marked AC2 HRP conventional or a different coupled antibody as presented above marked AC2 HRP new.

TABLE 13 intensity of the coloration obtained as a function of the coupled antibody and the LH concentration of the plasmas

| | AC2 HRP | | | | | | | |
|---|---|---|---|---|---|---|---|---|
| | Coupled antibody identical to that of example 1 (AC2 HRP) | | | | Different coupled antibody (AC2 HRP new) | | | |
| | LH (ng/ml) | | | | | | | |
| | 0 | 1 | 3.5 | 10 | 0 | 1 | 3.5 | 10 |
| Signal intensity | 5.77 | 8 | 27.45 | 32.9 | 7.87 | 15.73 | 37.78 | 55.16 |

Regardless of which peroxidase-coupled antibody was used, a colored signal was observed proportional to the LH concentration of the plasmas (FIG. 16 and Table 13 above). At a concentration of 10 µg/ml, the new peroxidase-coupled anti-LH antibody (AC2 HRP new) gives a higher color intensity but generates a slight nonspecific signal, signal intensity of 7.87 units, visible to the eye. In contrast, the AC2 HRP used in example 1 does not induce any background noise detectable to the eye with a signal intensity of 5 units.

In a second case, two commercial polyclonal anti-LH antibodies, in the form of immune sera, were used in order to be fixed on the test surface. It is the anti-bovine LH antibody marketed by the company US Biologicals Cat No. L7500-04P, batch No. L11010677, immune serum diluted 400 000 times, and the anti-porcine LH antibody marketed by the company US Biologicals Cat No. L7500-02H, Batch No. L11100302, immune serum diluted 100 times.

Two plasmas from cow or from sow at 0 and 5 ng/ml of LH obtained after centrifugation of blood samples, were used as samples. The coupled anti-LH antibody was that used in example 1 mentioned above (AC2 HRP) and was prepared at 10 µg/ml in PBS-FCS at 50% ($K_2HPO_4/KH_2PO_4$ 0.01 M-NaCl 0.15M, pH 7.4) (powders marketed by VWR, ref. 26930.293, 26936.293, 27810.295) comprising 50% (by volume) of FCS (fetal calf serum marketed by Lonza, reference 14-801F). The developer used was Membrane TMB marketed by KPL under the reference 50-77-18 diluted to half in citrate buffer ($NaCH_3CO_2/CH_3COOH$ 0.03M, pH5, (VWR, reference 27652.298 and Carlo Erba Reagents, reference 302 002).

Figure 17:
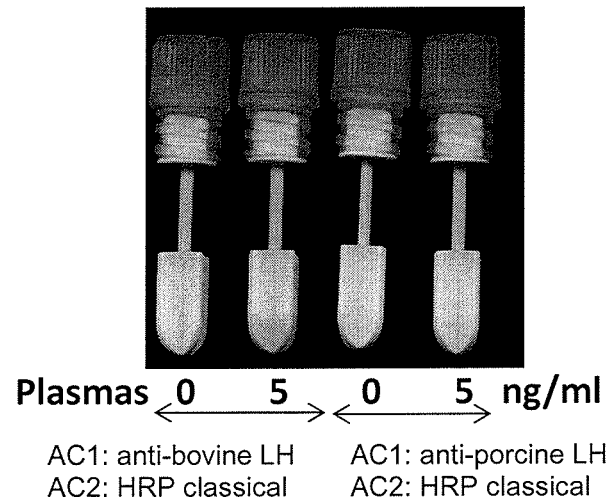
FIG. 17 shows a photograph of sticks after application of the method of the invention with samples of bovine plasmas comprising a concentration of 0 or 5 ng/ml of LH as a function of the antibody fixed on the test surface, namely an anti-bovine LH antibody (AC1: anti-bovine LH) or an anti-porcine LH antibody (AC1: anti-porcine LH) produced in the rabbit.

The results are presented in FIG. 17 and Table 14 below. FIG. 17 shows a photograph of sticks after application of the method of the invention with bovine plasma samples comprising an LH concentration of 0 or 5 ng/ml as a function of the antibody fixed on the test surface, namely a rabbit anti-bovine LH antibody (AC 1: anti-bovine LH) or a rabbit anti-porcine LH antibody (AC1: anti-porcine LH).

TABLE 14 intensity obtained as a function of the anti-LH antibody 1

| | AC1 commercial | | | |
|---|---|---|---|---|
| | anti-bovine LH | | anti-porcine LH | |
| LH (ng/ml) | 0 | 5 | 0 | 5 |
| Signal intensity | 5.88 | 24.18 | 5.4 | 11.23 |

As was demonstrated, no visual intensity of coloration (below 6) was obtained with the samples without LH and therefore a nonspecific signal is not produced. Moreover, a visual coloration of the test surface was obtained with the two antibodies in the test with a plasma comprising 5 ng/ml of LH. However, the intensity was lower, but perfectly visible, i.e. above 6 densitometry units in the case of anti-porcine LH AC1.

Finally, the stick was prepared using a fixed antibody and an enzyme-coupled antibody that were different from example 1: the fixed antibody AC1 was specific to bovine LH, it was the antibody marketed by the company US Biologicals Cat No. L7500-04P, batch No. L11010677, immune serum diluted 400 000 times and the antibody coupled to the enzyme, peroxidase, was an anti-bovine LH antibody produced in the rabbit and coupled to peroxidase (AC2 HRP new) according to the method described in "Techniques Immuno-enzymatiques" Therese Ternynck and Stratis Avrameas, (editions INSERM, 1987) [1]. The antibody was produced by the supplier Eurogentec (Belgium) by its method "Standard antiprotein packages 28-day Speedy in Rabbit" (brand name) from purified bovine LH. The peroxidase-coupled antibody used in example 1 (AC2 HRP conventional) was also used for comparison.

Figure 18:
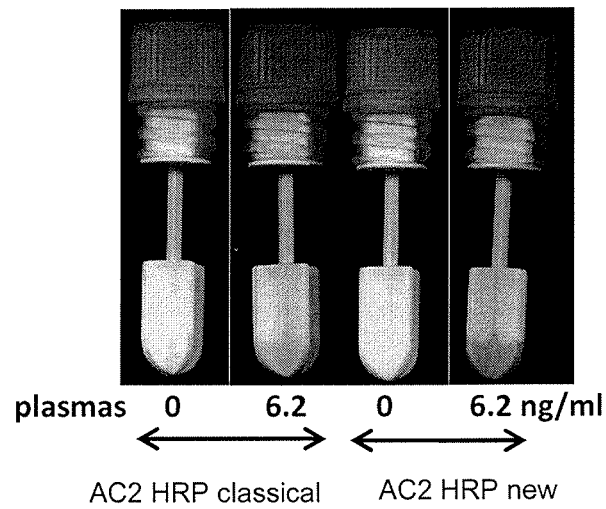
FIG. 18 shows a photograph of sticks after application of the method of the invention with samples of bovine plasmas comprising a concentration of 0 or 6.2 ng/ml of LH as a function of the enzyme-coupled anti-LH antibody used, namely an anti-ovine LH antibody produced in the horse (AC2 HRP conventional) or a polyclonal anti-porcine LH antibody produced in the rabbit (AC2 HRP new).

FIG. 18 shows a photograph of sticks after application of the method of the invention with samples of bovine plasmas comprising a concentration of 0 or 6.2 ng/ml of LH as a function of the enzyme-coupled anti-LH antibody, namely an anti-ovine LH antibody produced in the horse (AC2 HRP conventional) and a polyclonal anti-porcine LH antibody produced in the rabbit (AC2 HRP new).

TABLE 15

| | intensity obtained as a function of the peroxidase-coupled anti-LH antibody | | | |
|---|---|---|---|---|
| | AC2 HRP conventional | | AC2 HRP new | |
| LH (ng/ml) | 0 | 6.2 | 0 | 6.2 |
| Signal intensity | 4.34 | 24.76 | 2.45 | 54.83 |

These results, repeated in three independent experiments, all therefore clearly demonstrate that the method of the invention using a PBS buffer comprising FCS, for contacting with the test surface on which an anti-LH antibody is fixed and for preparing the enzyme-coupled anti-LH antibody, and use of Membrane TMB as substrate, advantageously makes it possible to obtain a test that is sensitive and functional, regardless of which antibodies are used.

In the two series of peroxidase-coupled antibodies (AC2 HRP), an intense colored signal was obtained, equivalent to the plasma with 6.2 ng/ml (Table 15, FIG. 18) and no color (no background noise) to the negative plasma with 0 ng/ml of LH (Table 15, FIG. 18). The visual reading of the results of the tests is therefore the same regardless of which combination of the antibodies is used.

This example therefore clearly demonstrates that the method of the invention advantageously permits visual detection of the LH peak with increased sensitivity and specificity.

Moreover, the kit for carrying out the method makes it possible to obtain a test that is reliable and sensitive.

Example 3

Application of the Method of Detecting the LH Peak in Bovines in Various Biological Media In this example, the method of detecting the LH peak was used with various biological samples: blood, plasma and vaginal mucus obtained from the bovine species. The tests were carried out for cows of various breeds: Holstein, Montbéliarde, Charolais and Blonde d'Aquitaine.

In each test, the results obtained with the method of the invention were systematically correlated with a quantitative ELISA assay performed on the same samples using the kit LH DETECT (registered trademark) (ReproPharm SA, France). For presentation of the results given below, the visual reading of the tests was validated by densitometric quantification of the color of the sticks. For this, the sticks are scanned with an EPSON Scanner (Perfection 1200 PHOTO) and then the intensity of the color obtained on each of them is quantified by densitometry with the "Scion Image" software (Scion Incorporation). This quantification is expressed in units of density.

Blood was collected beforehand either by taking blood using a heparinized Vacutainer from the caudal or jugular vein, or by scarification of the ear. When the sample was obtained from the ear, the cow was restrained with a neck yoke and its head was held in the lateral position with a halter, then, on the outer surface of the ear, the sample was taken following division of the lower vein. The sampling zone was cleaned with alcohol beforehand and rubbed to make the veins swell. A stylet with width of 5 mm (Goldenrod Animal Lancet, manufacturer MEDIPOINT) was positioned perpendicularly to the skin while holding the ear. Pressure was applied upstream of the vein in order to increase its volume. A tube was then positioned under the cut and the blood flowed into it. Bleeding was stopped by applying pressure on the sampling zone.

In the case of scarification, 4 to 5 drops of blood were recovered in tube No. 1 of the kit as described in example 5 below. This was carried out using a stylet with width of 5 mm (Goldenrod Animal Lancet, manufacturer MEDIPOINT).

a) Example of Detecting the Preovulatory LH Peak in the Blood in the Holstein Cow This example presents the results obtained on the farm, on a representative Holstein cow, on the 19th day of its sexual cycle, at the end of the luteal phase. The blood samples were collected every 30 minutes from injection of 2 ml of a GnRH analog, Cystoréline (gonadoliberin 0.05 mg/ml, CEVA Santé Animale).

For each sample, the LH peak was detected using the kit from example 5 below, with the following procedure:

The sample was obtained as described above, then the tubes of the kit in example 5 were taken out of the freezer 30 min before use.

The first tube (tube 1) was taken (stopper without colored disk) and the stick was removed from the tube. The stick was balanced on the stopper so as not to soil the end of the stick.

The blood sample was collected as described above. About 5 drops of blood were collected in tube 1 up to the bottom edge of the label and then the stick was screwed back onto this tube. The whole was left to incubate for at least 15 min at room temperature, 25° C., in the vertical position, with the end of the stick immersed in the blood.

The stick was then withdrawn and was shaken to remove the excess blood before being immersed in the washing pot (pot with WHITE stopper) containing 50 ml of PBS ($K_2HPO_4$/$KH_2PO_4$ 0.01 M-NaCl 0.15M, pH 7.4) and washed vigorously in the liquid with a circular motion, for 10 seconds. The stick was shaken after washing to remove the excess liquid.

The second tube comprising the reagent, i.e. the peroxidase-coupled anti-LH antibody (tube 2) (stopper labeled with a YELLOW disk), was opened by unscrewing the stopper and the stick was screwed in its place. The whole was left to incubate for at least 15 min at room temperature, 25° C., in the vertical position (with the end of the stick immersed in the reagent).

The stick was withdrawn and then shaken to remove the excess reagent before being immersed in the washing pot comprising 50 ml of PBS ($K_2HPO_4$/$KH_2PO_4$ 0.01 M-NaCl 0.15M, pH 7.4) (pot with WHITE stopper) and washed for 10 seconds, moving it vigorously in the liquid with a circular motion. The stick was shaken after washing to remove the excess liquid.

The third tube comprising a developer (tube 3) was opened by unscrewing the stopper and the stick was screwed in its place. The whole was left to incubate for at least 5 min at room temperature in the vertical position (with the end of the stick immersed in the developer).

The stick was unscrewed and reading and interpretation were carried out as described below, together with measurement of color intensity as described above and a quantitative ELISA assay was performed on the same samples using the kit LH DETECT (registered trademark). If the end of the stick is BLUE: the test is POSITIVE and indicates the presence of an LH peak. The cow must be inseminated about 12 hours later. If the end of the stick is white: the test is NEGATIVE and indicates absence of an LH peak.

Figure 19:
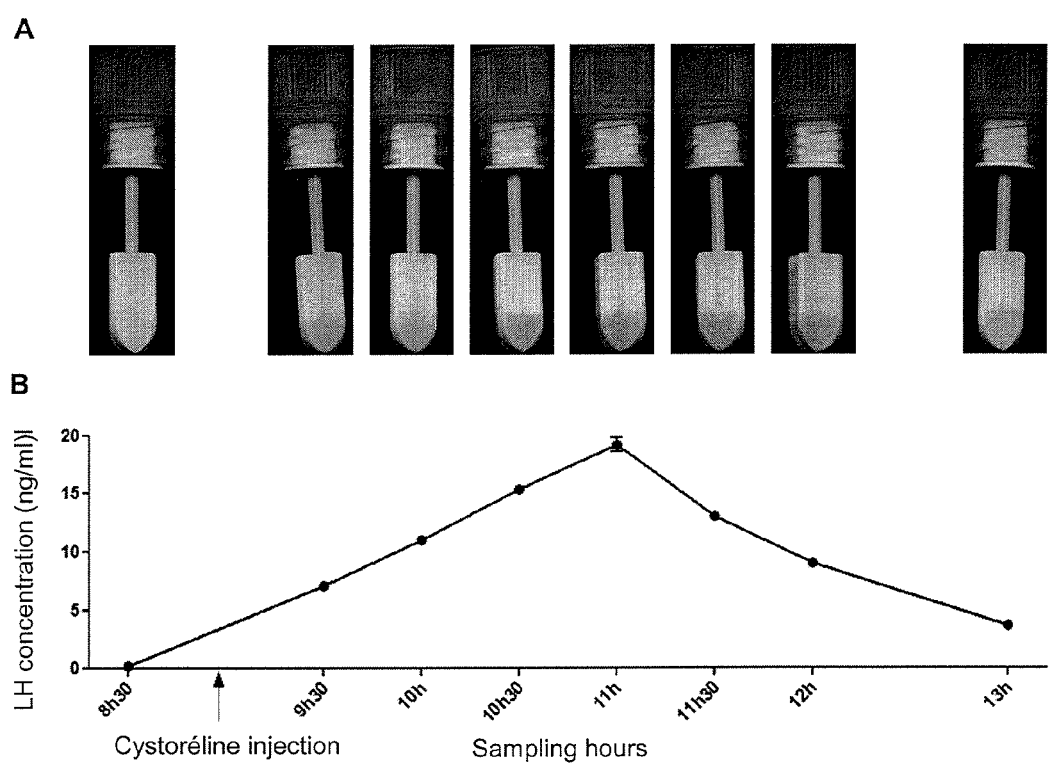
FIG. 19 A shows photographs of sticks obtained after application of the method as a function of the LH concentration in the blood of a Holstein cow taken at different times.

The results obtained are presented in FIG. 19. FIG. 19 A shows photographs of sticks obtained after application of the method on the various blood samples obtained from the cow.

FIG. 19 B shows a diagram of the LH concentration in ng/ml as a function of the time of obtaining the blood samples.

The same blood samples were analyzed qualitatively with the present kit (FIG. 19A) and quantitatively with LH DETECT (registered trademark) (FIG. 19B). The values of the colored signal of the sticks and the concentrations of LH measured with LH DETECT (registered trademark) are shown in Table 15.

TABLE 15 values of the colored signal of the sticks and of the LH concentration measured with LH DETECT (registered trademark)

| | Sampling time | | | | | | | |
|---|---|---|---|---|---|---|---|---|
| | 8 h 30 | 9 h 30 | 10 h | 10 h 30 | 11 h | 11 h 30 | 12 h | 13 h |
| Signal intensity | 4.8 | 26.3 | 34.2 | 38.9 | 42.1 | 38.7 | 29.3 | 21.2 |
| Concentration of LH (ng/ml) | 0.2 | 7.1 | 11.0 | 15.3 | 19.2 | 13.0 | 9.0 | 3.7 |

As demonstrated in FIG. 19 and Table 15, a parallel increase in concentration and in the colored signal of the sticks from 9 h30 to 11 h and then a decrease until 13 h were observed. Before the injection of Cystoréline, at 8 h30, the concentration is very low, and correlates very well with the stick, which remained white. The values of the LH concentrations measured quantitatively have a secretion profile identical to the evolution of the intensity of the colored signal observed on the sticks, with a maximum detected at 11 h and a minimum at 13 h.

The qualitative results obtained with the kit for detecting the LH peak therefore show a perfect correlation with the quantification of LH measured with the kit LH DETECT (registered trademark). These results were repeated on a population of 70 Holstein, Montbéliarde, Charolais, and Blonde d'Aquitaine cows. A correlation of 100% was obtained for all the breeds and validates the use of the present kit, in the field, for detecting the preovulatory LH peak.

b) Example for Detecting the Preovulatory LH Peak in the Blood and the Vaginal Mucus of a Holstein Cow This example was carried out on the farm, on a representative Holstein cow, which had received superovulation treatment for production of embryos.

Before the treatment, a CRESTAR SO implant (Centravet, France) was inserted on the 8th day of the sexual cycle and was removed in the evening of the 12th day.

The superovulation treatment was started on the 10th day of the cycle and was carried out according to the manufacturer's instructions. It consisted conventionally of 8 injections of 1.75 ml-1.75 ml-1.5 ml-1.25 ml-1.25 ml-1 ml-0.75 ml-0.75 ml of Stimufol (registered trademark of the company ULg FMV PhR, Belgium) respectively, by the intramuscular route, 12 hours apart (FSH1 to FSH8) and spread over four days from D10 to D13. An intramuscular injection of 3 ml of Prosolvin (registered trademark of the company Virbac, France) was also performed on FSH5.

Samples of blood and of vaginal mucus were obtained on the 13th day at 7H-13H-19H, on the 14th day at 7H-11 h-16H and on the 15th day at 7H.

The vaginal mucus was collected using a sterile syringe of 20 or 50 ml, attached to a sterile catheter (reference GAI 405, marketed by the company Centravet, France). The sample is then recovered in 1 ml (milliliter) of PBS pH 7.4 ($K_2HPO_4$/ $KH_2PO_4$ 0.01 M-NaCl 0.15M; supplier VWR, ref. 26930.293, 26936.293 and 27810.295).

The blood and the vaginal mucus were collected at the same time point so as to be able to compare the kinetics of appearance of the LH peak in the two media.

The samples of blood and of mucus were analyzed qualitatively, i.e. the signal intensity was measured by the aforementioned method and quantitatively with the assay kit LH DETECT (registered trademark).

Figure 20:
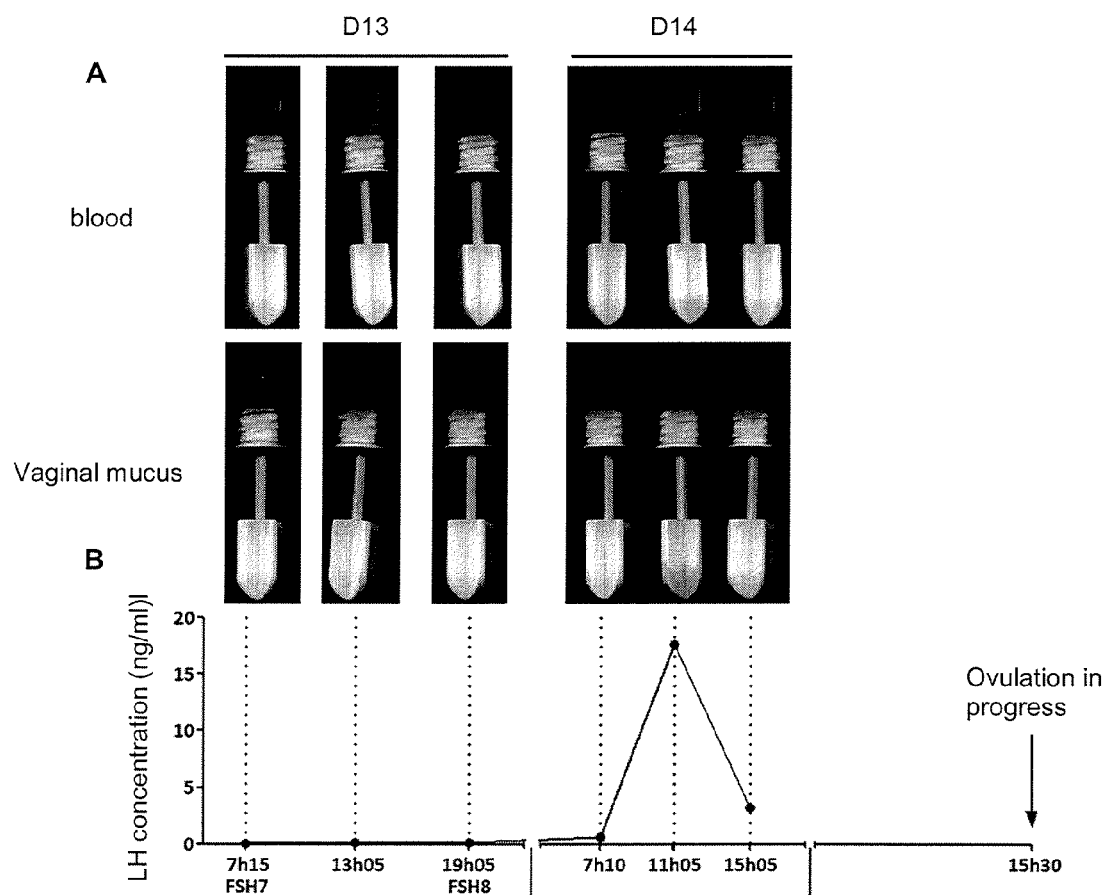
FIG. 20 A shows photographs of sticks obtained according to the method of the invention from blood or from vaginal mucus of a cow given a superovulation treatment, on the thirteenth (D13) and on the fourteenth (D14) day of the cycle.

The results are presented in FIG. 20 and Table 16.

FIG. 20 A shows photographs of sticks obtained according to the method of the invention from samples of blood and of vaginal mucus from the cow on the thirteenth (D13) and on the fourteenth (D14) days of the cycle.

FIG. 20 B shows the LH concentration in ng/ml as a function of time in hours of the various samples obtained on the thirteenth day (D13), and on the fourteenth day (D14) and fifteenth day (D15).

TABLE 16

Values of the LH concentration and intensity of the colored signal of the sticks obtained from the various samples of blood and of vaginal mucus

| samples | LH concentration | Quantification of the colored signal of the sticks | |
|---|---|---|---|
| hour and date | (ng/ml) | Blood | Vaginal mucus |
| 7 h D 13 | 0.1 | 5.5 | 7.4 |
| 13 h D 13 | 0.13 | 5.3 | 2.2 |
| 19 h D 13 | 0.14 | 5.6 | 6.3 |
| 7 h D 14 | 0.67 | 5.7 | 7.3 |
| 11 h D 14 | 17.57 | 13.4 | 22.7 |
| 15 h D 14 | 3.27 | 5.8 | 11.5 |

For the samples taken on D13, no colored signal was observed on the sticks, whether in blood or in vaginal mucus. These results correlate with the very low values of plasma LH concentration, thus demonstrating that there is no false positive. On D14, an intense colored signal was observed on the sticks at 11H both with the blood and with the vaginal mucus, corresponding to the maximum of the LH secretion peak (17.57 ng/ml) measured with LH DETECT (registered trademark). A weaker colored signal was observed on the sticks at 15H on the blood and the vaginal mucus, corresponding to the end of the LH secretion peak (3.27 ng/ml) measured with LH DETECT (registered trademark). Ovulation was detected by ultrasonography on the next day on D15, clear evidence of a functional LH peak 24 hours earlier, on D14.

These results demonstrate very clearly that the method of the invention and the kit for application of this method make it possible to detect the preovulatory LH peak from a sample of whole blood but also from a sample of vaginal mucus. Appearance of the preovulatory LH peak is found simultaneously in the two samples.

Advantageously, the method and the kit of the invention make it possible to detect very easily, on the farm, the preovulatory LH peak and thus constitute a tool for improving artificial insemination practice in the cow. This kit is thus a tool for predicting the moment of ovulation (occurring, in the cow, 24 hours after the LH peak) thus permitting better planning of the operation of artificial insemination in animal husbandry.

The kit can be used as an aid in superovulation treatments to optimize fertilization and obtain a large number of good-quality embryos that are transferable.

Example 4

Application of the Method of Detecting the LH Peak in the Pig in Various Biological Media The method of detecting the LH peak was applied using various samples from the pig species: blood, plasma, serum and vaginal mucus. The tests involved multiparous Large-White sows bred in batches, in intensive farming conditions.

In each test, the results obtained with the method of the invention were systematically correlated with a quantitative ELISA assay performed on the same blood samples using the kit LH DETECT (registered trademark) (ReproPharm SA, France). For presentation of the results given below, the visual reading of the tests was validated by densitometric quantification of the color of the sticks. For this, the sticks were scanned using an EPSON Scanner (Perfection 1200 PHOTO) and then the color intensity obtained on each of them is quantified by densitometry with the "Scion Image" software (Scion Incorporation). This quantification is expressed in units of density.

The blood samples were obtained using heparinized Vacutainers from the jugular vein.

The vaginal mucus was collected using an insemination tube (reference Sonde Kobi, Cobiporc, France). The mucus sample was then recovered in 1 ml (milliliter) of PBS pH 7.4 ($K_2HPO_4/KH_2PO_4$ 0.01 M-NaCl 0.15M; supplier VWR, ref. 26930.293, 26936.293 and 27810.295).

The blood and vaginal mucus were collected at the same time point so as to be able to compare the kinetics of appearance of the LH peak in the two biological media.

The protocol for breeding in batches was as follows: the sows were weaned 28 days after farrowing. Weaning indicates the start day of a new cycle (D0). The samples of blood and of mucus were taken at 9 h and 16 h30 every day from D3 to D7. In parallel, detection of estrus was performed at these same times, as well as ultrasonography of the ovaries, for dating ovulation.

For each sample, detection of the LH peak was performed using the kit in example 5 below.

Figure 21:
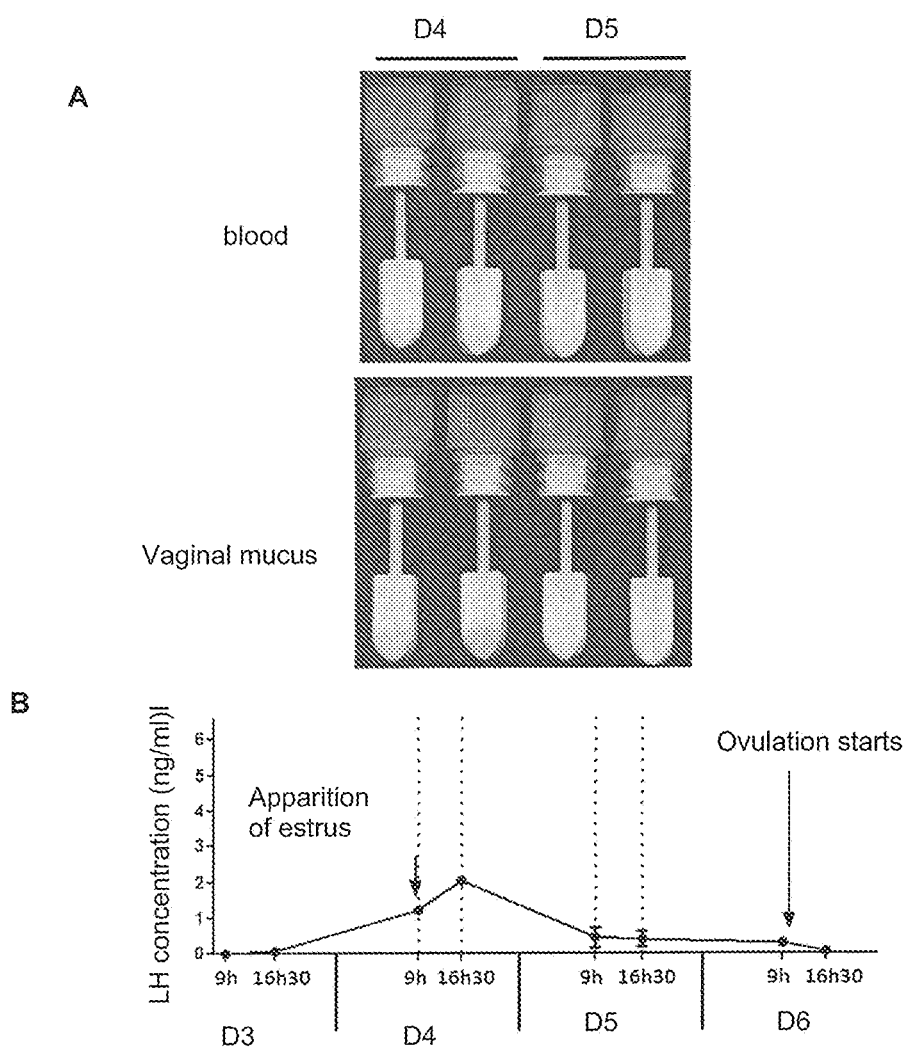
FIG. 21 A shows photographs of sticks obtained according to the method of the invention from blood or from vaginal mucus of a sow (sow 1) on the third day (D3), fourth day (D4) and fifth day (D5) after weaning.

The results obtained with a first sow (sow 1) are shown in FIG. 21 and in Table 17 below.

FIG. 21 A shows photographs of sticks obtained according to the method of the invention from blood or vaginal mucus of sow 1 on the fourth day (D4) and fifth day (D5) after weaning.

FIG. 21 B shows the plasma LH concentration in ng/ml as a function of time in hours on the fourth day (D4) and fifth day (D5) after weaning.

TABLE 17

Values of the LH concentration and intensity of the colored signal of the sticks obtained with the various samples of blood and of vaginal mucus.

| samples | LH concentration | Quantification of the colored signal of the sticks | |
|---|---|---|---|
| hour and date | (ng/ml) | Blood | Vaginal mucus |
| 9 h D 4 | 9.27 | 10.52 | 20.33 |
| 16 h 30 D 4 | 13.45 | 12.12 | 26.92 |
| 9 h D 5 | 8.79 | 7.35 | 5.89 |
| 16 h 30 D 5 | 5.8 | 4.29 | 4.72 |

In the two biological media, the sticks showed a colored signal on D4, indicating start of the LH peak at 9 h and maximum secretion at 16 h30 for which the colored signal was the most intense in the blood and in the vaginal mucus. On D5, the sticks gave a slight colored signal at 9 h and then no color at 16 h30 indicating return to baseline LH concentration. This qualitative detection is perfectly correlated with the concentration values obtained by the quantitative assay.

The validity of the results obtained with the method of the invention was confirmed by the ultrasonography results obtained, indicating ovulation at 9 h on D6, or 48 h after the start of the LH peak.

Figure 22:
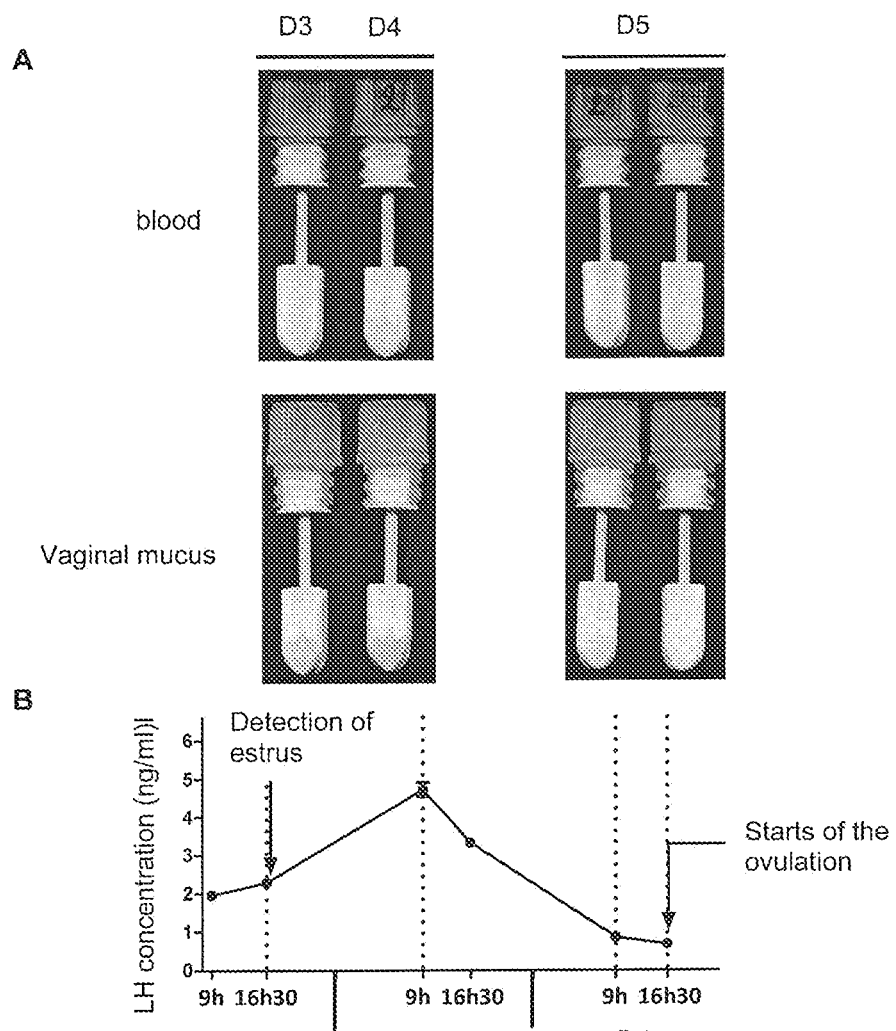
FIG. 22 A shows photographs of sticks obtained according to the method of the invention from blood or from vaginal mucus of a sow (sow 2) on the third day (D3), fourth day (D4) and fifth day (D5) after weaning.

The results obtained with a second sow (sow 2) are shown in FIG. 22 and Table 18.

FIG. 22 A shows photographs of sticks obtained according to the method of the invention from blood or vaginal mucus of sow 2 on the third day (D3) or fourth day (D4) and fifth day (D5) after weaning.

FIG. 22 B shows the plasma LH concentration in ng/ml as a function of time in hours on the third day (D3), fourth day (D4) and fifth day (D5) after weaning.

TABLE 18

Values of the LH concentration and intensity of the colored signal of the sticks obtained with the various samples of blood and of vaginal mucus

| samples | LH concentration | Quantification of the colored signal of the sticks | |
|---|---|---|---|
| hour and date | (ng/ml) | Blood | Vaginal mucus |
| 16 h 30 D 3 | 2.5 | 10.59 | 26.43 |
| 9 h D 4 | 4.8 | 13.93 | 47.78 |
| 16 h 30 D 4 | 3.5 | | |
| 9 h D 5 | 0.8 | 1 | 15.34 |
| 16 h 30 D 5 | 0.5 | 0.48 | 0.06 |

In this example, both in blood and in vaginal mucus, appearance of a colored signal was demonstrated on the sticks at 16 h30 on D3 which is intensified at 9 h on the fourth day (D4), then decreases at 9 h on the fifth day (D5) and is cancelled at 16 h30 on the fifth day (D5) (FIG. 22 A). These data are perfectly correlated with the values for plasma LH concentrations determined with the quantitative assay (FIG. 22 B). The method of the invention makes it possible to obtain a colored signal over an interval of 36 hours particularly in the vaginal mucus, which correlates very well with the average duration of an LH peak in the sow, which varies between 36 and 48 hours.

The physiological validity of the results obtained with the method of the invention is also supported by the results of ultrasonography, indicating ovulation at 16 h30 on the fifth day (D5), or 48 h after the start of the LH peak.

These results all show that the method of the invention permits detection of the preovulatory LH peak, in animal husbandry, both in the blood and in the vaginal mucus of the sow.

Moreover, as demonstrated in this example, the method of the invention and the kit of the invention advantageously permit visual detection of the LH peak.

Example 5

Manufacture of a Kit for Applying the Method of the Invention

In this example, the kit comprises:
  a stick comprising test surfaces, ready for use in a heparinized tube,
  a tube comprising the solution of conjugate, namely a buffer solution with an anti-LH antibody coupled to horseradish peroxidase (conjugated antibody), and a tube comprising a solution comprising the substrate of horseradish peroxidase, namely Membrane TMB called substrate.

Equipment Used:
Immunostick marketed by the company NUNC, and three cryotubes with screwed stopper marketed by the company NUNC.

All the buffers used in the manufacture of the kit were prepared in milliQ water.

The various elements were prepared according to the methods described below.

Preparation of the Heparinized Tubes:

Preparation by mixing 100 µl of a heparin sodium solution (Choay Heparin, at 5000 IU/ml registered trademark, marketed by Sanofi Aventis) in 900 µl of PBS filtered on a filter with porosity of 0.22 µm (supplier Millipore; reference GSWP04700).

Distribution of 6 IU of heparin sodium per tube (cryotube NUNC, Dutscher, ref. 055003) or 12 µl of solution at 500 IU/ml.

Drying for 3 hours in a stove at 37° C.

Storage at 4° C. or at −20° C.

Preparation of the Sticks

Coating of the stick with 250 µl of rabbit anti-bovine LH antibody purified on a Protein A Sepharose column from an immune serum produced in the rabbit by the supplier Eurogentec (Belgium) according to the method "Standard antiprotein packages 28-day Speedy in Rabbit" (brand name) called hereinafter AC1 prepared at 20 µg/ml in buffer $NaHCO_3$/$Na_2CO_3$ 0.1 M pH 9.6 containing 0.05 vol % of ProClin300 (registered trademark) marketed by the company Sigma-Aldrich, ref. 48912-U.

In another embodiment the anti-LH antibody (AC1) was a rabbit anti-porcine LH antibody, it is the antibody produced for example by immunization of rabbits by the method described for example in the reference "Radio-immunoassay of the plasma luteinizing hormone in the sheep. Development of the assay technique", Pelletier J., Kann G., Dolais J., Rosselin G., *C. R. Acad. Sc. Paris,* 1968 June; 266: 2291-2294 [5]. It was the method comprising for example three injections of 200 µg of purified porcine LH marketed by the company Tucker Endocrine Research Institute LLC TUENRE (Atlanta, USA), which were performed every two weeks, followed by ten boosters with 100 µg of purified porcine LH carried out every five weeks. Blood samples were taken six and nine days after each booster and 40 ml of blood was recovered. Starting from the blood samples, the rabbit antibodies were purified by affinity chromatography on Protein A Sepharose gel according to the method described in "Techniques Immuno-enzymatiques" Thérèse Ternynck and Stratis Avrameas, éditions INSERM, 1987 [1]. Coupling of the antibody was carried out by the method described in "Techniques Immuno-enzymatiques" Thérèse Ternynck and Stratis Avrameas, éditions INSERM, 1987 [1]. Incubation for one hour at 37° C., then 18 hours at 4° C. Drying of the stick by shaking.

"Surcoating" of the stick in 900 µl of PBS with addition of fetal calf serum (FCS) 50% (supplier LONZA, reference 14-801 F) for 1 hour at 37° C.

Drying of the stick by shaking.

Drying of the stick in the vertical position in the stove at 37° C. for 3 hours.

Storage of the stick at 4° C. or at −20° C. in a dried heparinized tube.

Preparation of the Reagent Comprising the Solution of Conjugate (Tube No. 2)

Preparation of the horse anti-ovine LH antibody coupled to horseradish peroxidase (HRP), called hereinafter AC2 HRP at 10 µg/ml in PBS FCS 50 vol % containing 0.05 vol % of ProClin300 (registered trademark). Incubation for 50 minutes at 37° C. and distribution of 300 µl per cryotube. Storage at 4° C. or at −20° C.

This antibody was produced from an antibody purified on a Protein G Sepharose column from a horse serum immunized against purified ovine LH. It was in particular the anti-ovine LH antibody produced in the horse described in French patent FR No. FR90 06863, patent No. FR 2 662 804. This purified antibody was then coupled according to the protocol described in Techniques Immuno-enzymatiques of Thérèse Ternynck and Stratis Avrameas, éditions INSERM, 1987 [1].

In another embodiment it is the antibody produced for example by immunization of rabbits according to the method described in the reference "Radio-immunoassay of the plasma luteinizing hormone in the sheep. Development of the assay technique", Pelletier J., Kann G., Dolais J., Rosselin G., *C. R. Acad. Sc. Paris,* 1968 June; 266: 2291-2294 [5]. It was the method comprising for example three injections of 200 µg of purified porcine LH obtained from the company Tucker Endocrine Research Institute LLC TUENRE (Atlanta, USA), which were performed every two weeks, followed by ten boosters with 100 µg of purified LH carried out every five weeks. Blood samples were taken six and nine days after each booster and 40 ml of blood was recovered. Starting from the blood samples, the rabbit antibodies were purified by affinity chromatography on Protein A Sepharose gel according to the method described in "Techniques Immuno-enzymatiques" Thérèse Ternynck and Stratis Avrameas, éditions INSERM, 1987 [1]. Coupling of the antibody was carried out by the method described in "Techniques Immuno-enzymatiques" Thérèse Ternynck and Stratis Avrameas, éditions INSERM, 1987 [1]. The porcine LH was marketed by Tucker Endocrine Research Institute LLC TUENRE (Atanta, USA). The peroxidase used is marketed by Sigma under the reference P6782.

Preparation of the Tubes of Developer (Tube No. 3)

Dilution of Membrane TMB marketed by KPL under the reference 50-77-18 at 50 vol % in citrate buffer ($NaCH_3CO_2$) 0.03M adjusted to pH5 with acetic acid ($CH_3COOH$). Distribution of 300 µl of the mixture per cryotube.

Storage at 4° C. or at −20° C. protected from the light.

LIST OF REFERENCES

1. "Techniques Immuno-enzymatiques" [Immunoenzyme Techniques]. Thérèse Ternynck and Stratis Avrameas, éditions INSERM, 1987.
2. Immunobiology Charles A. Janeway, Paul Travers, Pierre L. Masson—2003—Medical; Janeway's Immunobiology, Kenneth Murphy, Paul Travers, Mark Walport, 2011, editions GS.
3. "Enzyme-linked immunosorbent assay (ELISA). Quantitative assay of immunoglobulin G", Engvall, E. and Perlman, P., *Immunochemistry,* 1971 September; 8(9): 871-4 PMID: 5135623.
4. "Enzyme-Linked Immunosorbent Assay" Goldsby, R. A., Kindt, T. J., Osborne, B. A. and Kuby, J., in *Immunology,* 5th edition (2003), pp. 148-150, W. H. Freeman, New York.
5. "Dosage radio-immunologique de l'hormone lutéinisante plasmatique chez le mouton. Mise au point de la technique de dosage" [Radio-immunoassay of the plasma luteinizing hormone in the sheep. Development of the assay technique], Pelletier J., Kann G., Dolais J., Rosselin G., *C. R. Acad. Sc. Paris,* 1968 June; 266: 2291-2294

6. La production d'embryons chez les bovins: quelles voies de recherche pour augmenter l'efficacité des traitements de super ovulation [The production of embryos in bovines: research trends for increasing the efficacy of superovulation treatments], Saumande J. *INRA Productions Animates,* 1995; 8(4), 275-283.

7. "Use of Norgestomet implant as an aid when superovulating low fertility dairy cattle", Ellington J E, Elefson E E, McCall R M. *Theriogenology,* 1987; 27, 227.

The invention claimed is:

1. A method of detecting the preovulatory Luteinizing Hormone (LH) peak in a biological sample obtained from mammals consisting of the following steps:
    (a) contacting a test surface comprising an anti-Luteinizing Hormone (anti-LH) antibody with a buffer solution comprising 5 to 50 vol % of fetal calf serum;
    (b) contacting said surface obtained in step (a) with a biological sample;
    (c) after step (b), rinsing the test surface in a washing solution;
    (d) contacting the test surface rinsed in step (c) with a buffer solution of conjugate comprising an enzyme-coupled anti-LH antibody and from 5 to 50 vol % of fetal calf serum;
    (e) after step (d), rinsing the test surface in a washing solution;
    (f) after step (e), contacting the test surface with a solution comprising a substrate of said enzyme, said substrate comprising 3,3',5,5'-tetramethylbenzidine membrane (Membrane TMB), wherein binding of said substrate and said enzyme causes a color change on the test surface that is proportional to the amount of LH present in the test sample; and
    (g) visually observing the color change on the test surface to detect the presence of LH in the biological sample.

2. The method as claimed in claim 1, in which the biological sample is selected from the group comprising blood, plasma, serum, vaginal mucus, saliva, urine, milk.

3. The method as claimed in claim 1, in which the washing solution used in steps (c) or (e) is or is not the same.

4. The method as claimed in claim 1, in which the washing solution used in steps (c) or (e) is selected from phosphate-buffered saline or water.

5. The method as claimed in claim 1, in which the mammal is a human or an animal.

6. The method as claimed in claim 1, in which the animal is selected from the group comprising bovines, pigs, sheep, goats, canines, and equines.

7. The method as claimed in claim 1, in which the mammal is a human.

8. The method as claimed in claim 1, in which the anti-LH antibody fixed on the test surface in step (a) is a polyclonal or monoclonal antibody selected from the group comprising anti-bovine LH antibody, anti-porcine LH antibody, anti-ovine LH antibody, anti-canine LH antibody, anti-feline LH antibody, anti-equine LH antibody, anti-camelid LH antibody, anti-human LH antibody.

9. The method as claimed in claim 1, in which the enzyme-coupled anti-LH antibody is a polyclonal or monoclonal antibody selected from the group comprising anti-bovine LH antibody, anti-porcine LH antibody, anti-ovine LH antibody, anti-canine LH antibody, anti-feline LH antibody, anti-equine LH antibody, anti-camelid LH antibody, anti-human LH antibody.

10. The method as claimed in claim 1, in which the anti-LH antibody is coupled to an enzyme selected from the group comprising the enzyme peroxidase, beta-galactosidase, glucose oxidase and alkaline phosphatase.

11. The method as claimed in claim 10, in which the enzyme is peroxidase.

12. The method as claimed in claim 11, in which the peroxidase is selected from the group comprising the peroxidases with heme or the peroxidases without heme.

13. The method as claimed in claim 1, in which step (b) and (d) of contacting is carried out for at least 5 minutes.

14. The method as claimed in claim 1, in which step (f) of contacting is carried out for at least 5 minutes.

15. The method as claimed in claim 1, in which the Membrane TMB is diluted in a citrate buffer with a dilution factor from ½ to 1/20.

16. The method as claimed in claim 1, in which the test surface is of plastic.

17. The method as claimed in claim 1, in which the biological sample is blood and step (b) of contacting is carried out in a heparinized tube.

18. The method as claimed in claim 1, in which said test surface is a stick comprising several test surfaces.

* * * * *